US008419780B2

(12) United States Patent
Bickley et al.

(10) Patent No.: US 8,419,780 B2
(45) Date of Patent: Apr. 16, 2013

(54) APPARATUS FOR SECURING AN IMPLANTABLE OBJECT TO BONE

(75) Inventors: Barry T. Bickley, North Andover, MA (US); Aldo M. Zovich, East Hampton, CT (US); Richard E. Zovich, Kinsington, CT (US)

(73) Assignee: Simplicity Orthopedics, Inc., North Andover, MA (US)

( * ) Notice: Subject to any disclaimer, the term of this patent is extended or adjusted under 35 U.S.C. 154(b) by 1376 days.

(21) Appl. No.: 10/554,379

(22) PCT Filed: May 10, 2004

(86) PCT No.: PCT/US2004/014640
§ 371 (c)(1),
(2), (4) Date: Oct. 25, 2005

(87) PCT Pub. No.: WO2004/100809
PCT Pub. Date: Nov. 25, 2004

(65) Prior Publication Data
US 2006/0074421 A1    Apr. 6, 2006

Related U.S. Application Data

(63) Continuation-in-part of application No. 10/246,304, filed on Sep. 18, 2002, now abandoned.

(60) Provisional application No. 60/468,829, filed on May 8, 2003, provisional application No. 60/323,347, filed on Sep. 18, 2001, provisional application No. 60/347,212, filed on Jan. 10, 2002, provisional application No. 60/374,534, filed on Apr. 22, 2002.

(51) Int. Cl.
    *A61B 17/58* (2006.01)

(52) U.S. Cl.
    USPC .......................................... 606/326; 606/286

(58) Field of Classification Search .................... 606/63, 606/66, 68, 218, 304, 313, 315, 321, 326, 606/291, 286, 280, 283, 902, 903, 905, 906, 606/314, 327; 623/17.15, 23.25; 411/80.1, 411/80.2, 80.5, 80.6, 214
See application file for complete search history.

(56) References Cited

U.S. PATENT DOCUMENTS

| 1,752,752 A | 4/1930 | Ogden |
| 2,307,179 A | 1/1943 | Whitehead |

(Continued)

FOREIGN PATENT DOCUMENTS

| CH | 645 168 A5 | 9/1984 |
| DE | G 89 08 858.1 | 1/1990 |

(Continued)

OTHER PUBLICATIONS

PCT Search Report and Written Opinion of the ISA for PCT/US2006/000932 dated May 8, 2005.

(Continued)

*Primary Examiner* — Brian Pellegrino
(74) *Attorney, Agent, or Firm* — Pandiscio & Pandiscio

(57) ABSTRACT

A fixation augmentation device (FAD) comprising a generally tubular body having a first end and a second end, said body having an opening adapted to receive a screw therein; a collar attached to the first end of said body, said collar having a non-circular shape and having an opening which is aligned with the opening in said body; and at least one flange disposed at the second end of said body, wherein said at least one flange is extendable from said body in response to a screw being inserted into the hole of said body.

25 Claims, 19 Drawing Sheets

U.S. PATENT DOCUMENTS

| | | | |
|---|---|---|---|
| 2,381,050 A | | 8/1945 | Hardinge |
| 3,174,387 A | | 3/1965 | Fischer |
| 3,232,163 A | | 2/1966 | Croessant |
| 3,473,222 A | | 10/1969 | Kester |
| 3,896,504 A | | 7/1975 | Fischer |
| 4,201,531 A | | 5/1980 | Schurman |
| 4,276,806 A | * | 7/1981 | Morel ............................ 411/41 |
| 4,312,612 A | | 1/1982 | Thompson |
| 4,484,570 A | | 11/1984 | Sutter et al. |
| 4,553,273 A | * | 11/1985 | Wu ................ 606/246 |
| 4,601,625 A | | 7/1986 | Ernst et al. |
| 4,611,581 A | | 9/1986 | Steffee |
| 4,716,893 A | | 1/1988 | Fischer et al. |
| 5,084,050 A | | 1/1992 | Draenert |
| 5,224,805 A | | 7/1993 | Moretti et al. |
| 5,324,292 A | * | 6/1994 | Meyers ........................ 606/301 |
| 5,356,435 A | | 10/1994 | Thein |
| 5,375,954 A | * | 12/1994 | Eguchi ........................ 411/80.2 |
| 5,601,558 A | | 2/1997 | Torrie et al. |
| 5,713,904 A | | 2/1998 | Errico et al. |
| 5,716,359 A | | 2/1998 | Ojima et al. |
| 5,725,529 A | | 3/1998 | Nicholson et al. |
| 5,871,485 A | | 2/1999 | Rao et al. |
| 5,899,938 A | | 5/1999 | Sklar et al. |
| 5,976,141 A | | 11/1999 | Haag et al. |
| 6,056,750 A | | 5/2000 | Lob |
| 6,206,881 B1 | | 3/2001 | Frigg et al. |
| 6,299,642 B1 | * | 10/2001 | Chan .............................. 606/63 |
| 6,355,044 B1 | * | 3/2002 | Hair .............................. 606/326 |
| 6,623,486 B1 | * | 9/2003 | Weaver et al. ................ 606/291 |
| 2001/0053913 A1 | * | 12/2001 | Freedland ...................... 606/73 |
| 2003/0065391 A1 | | 4/2003 | Re et al. |
| 2003/0074075 A1 | * | 4/2003 | Thomas et al. ............ 623/17.16 |
| 2004/0176767 A1 | | 9/2004 | Bickley et al. |
| 2006/0052787 A1 | | 3/2006 | Re et al. |

FOREIGN PATENT DOCUMENTS

| | | |
|---|---|---|
| DE | 4201531 | 7/1993 |
| DE | 298 23 395 | 9/1999 |
| EP | 0 089 298 A1 | 9/1983 |
| EP | 0 330 328 A1 | 8/1989 |
| EP | 0 596 829 A1 | 5/1994 |
| EP | 0 610 575 A3 | 8/1994 |
| EP | 1 018 321 A2 | 7/2000 |
| EP | 1 018 321 A3 | 4/2001 |
| GB | 2 266 246 A | 10/1993 |
| GB | 2 307 179 | 5/1997 |
| WO | WO 98/35635 | 8/1998 |
| WO | WO 9848738 A1 * | 11/1998 |
| WO | WO 02/085182 A2 | 10/2002 |
| WO | WO 03/047440 A2 | 6/2003 |
| WO | WO 2004/006792 A1 | 1/2004 |

OTHER PUBLICATIONS

Innovasive Deivces, "Technique for Tibial Fixation of ACL Grafts", Joseph H. Skar, M.D., 1999.

Scandius Biomedical; "TriTis Tibial Fixation System and Implant" Brochure from Scandius BioMedical, Inc. website http://www.scandius.com/documents/TriTisSSheetPlum3.pdf; Jan. 1, 2006

PCT Search Report and Written Opinion of the ISA for PCT/US2004/014640 dated Nov. 14, 2004.

Patent Search Report; Smith & Nephew Corporate Patents & Trade Marks Department; Search No. S1951; Search Title Osteoporotic Screw System; Report No. 2002032; Search Period 1970 to Mar. 26, 2002; two sheets.

Cook et al.: "Biomechanical Evaluation and Preliminary Clinical Experience with an Expansive Pedicle Screw Design;" Journal of Spinal Disorders; vol. 13, No. 3; Jun. 13, 2000; pp. 230-236.

Glatzmaier et al.; "Biodegradable Implants for Orthodontic Anchorage. A Preliminary Biomechanical Study;" European Journal of Orthodontics; vol. 18 No. 5 (1996); pp. 465 469.

Gualtieri et al.: "Biological and Mechanical Characteristics of the Interface Between a New Swelling Anchor and Bone;" Journal of Orthopeadic Research; vol. 18: The Journal of Bone and Joint Surgery, Inc.; pp. 494-499.

McKoy et al.; "An Expandable Anchor for Fixation in Osteoporotic Bone;" Journal of Orthopaedic Research; vol. 19 (2001) Jun. 15, 1998; 0736-0266/01; pp. 545-547.

Polly et al.; "Revision Pedicle Screws;" SPINE vol. 23, No. 12; © 1998, Lippincott-Raven Publishers; pp. 1374-1379.

Sklar; "Intrafix Technique for Tibial Fixation of ACL Grafts;" Innovasive Devices, Inc. P/N 900506, Rev. A; Aug. 2000; 5 sheets.

* cited by examiner

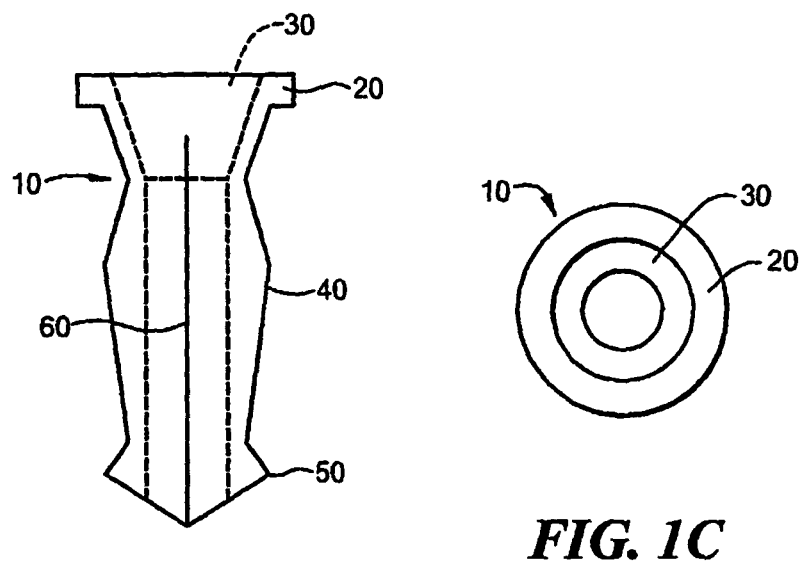
FIG. 1A
FIG. 1C
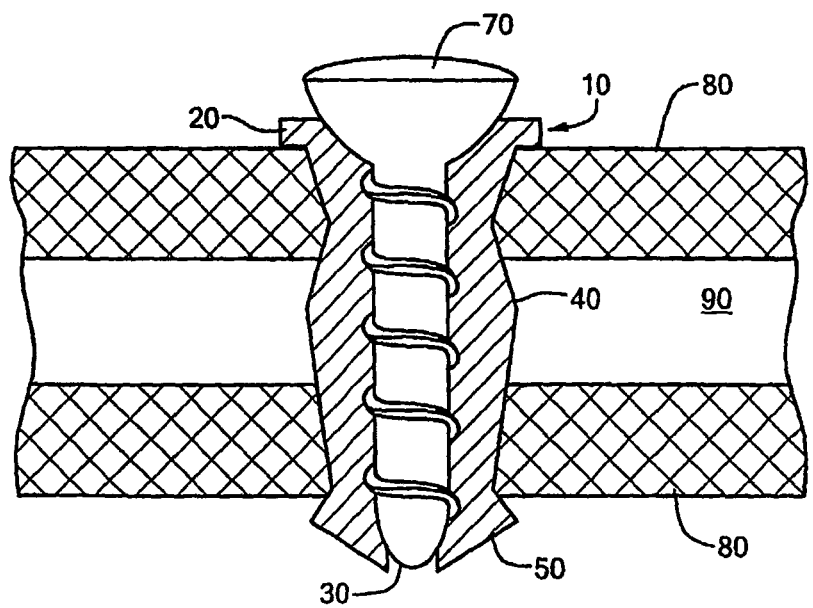
FIG. 1B

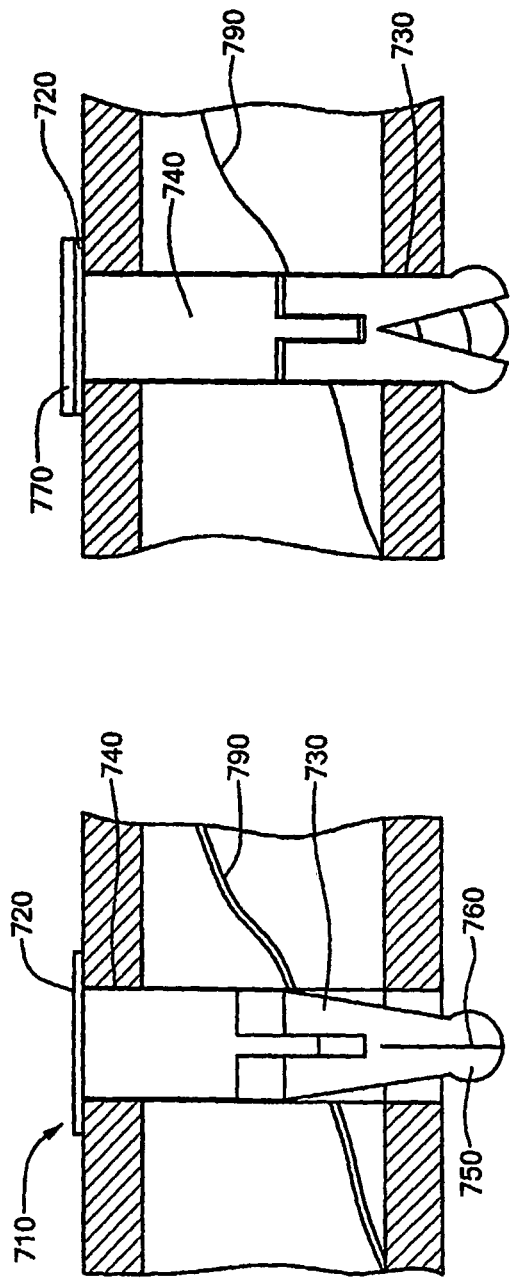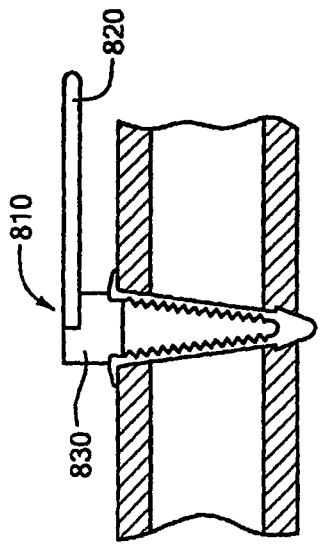
FIG. 7A
FIG. 7B
FIG. 8

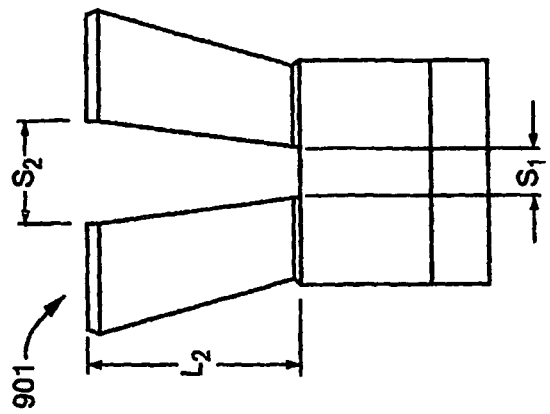
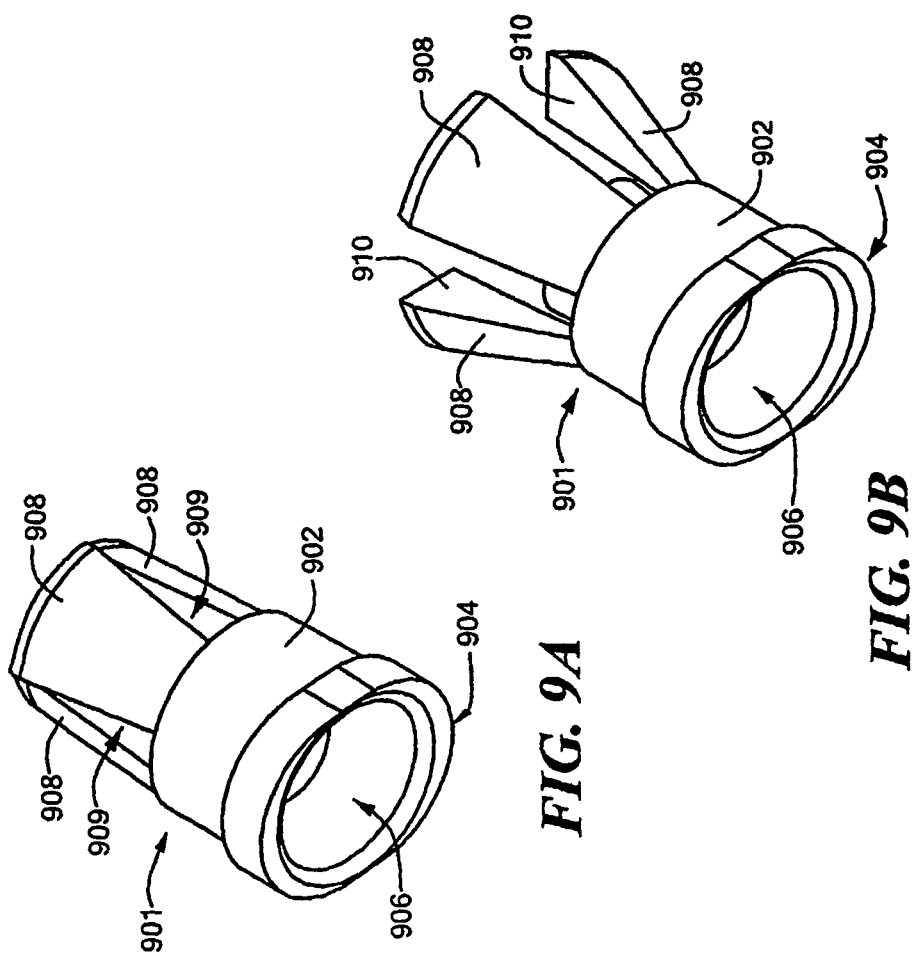

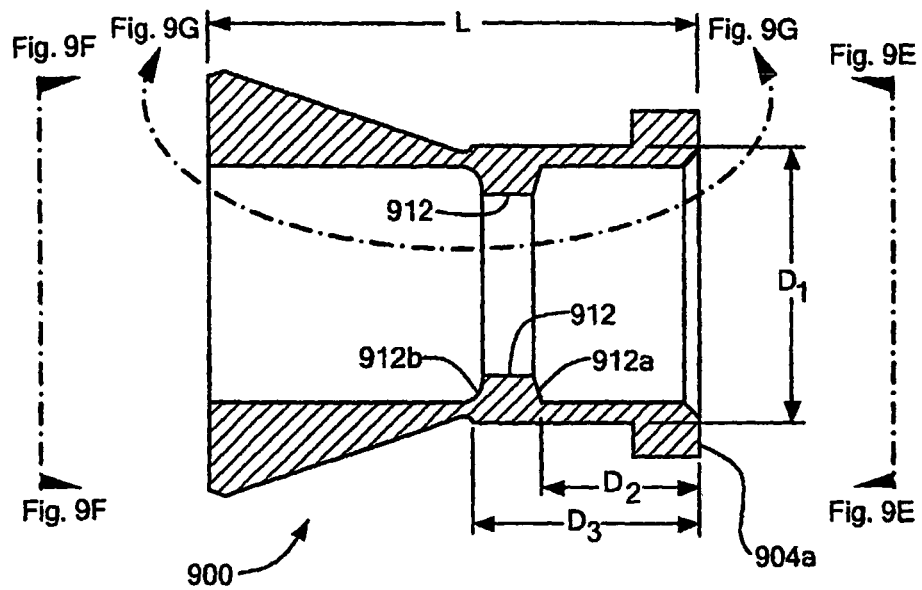
FIG. 9D
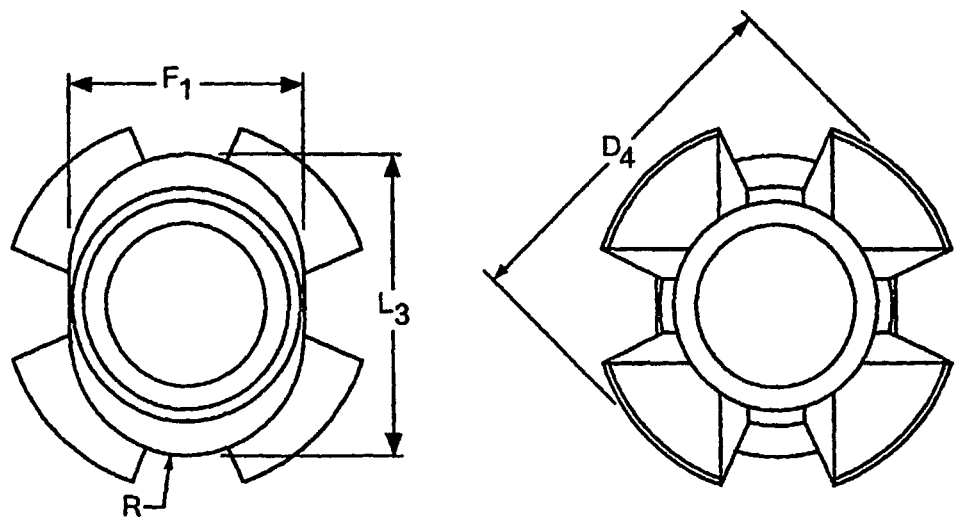
FIG. 9E   FIG. 9F

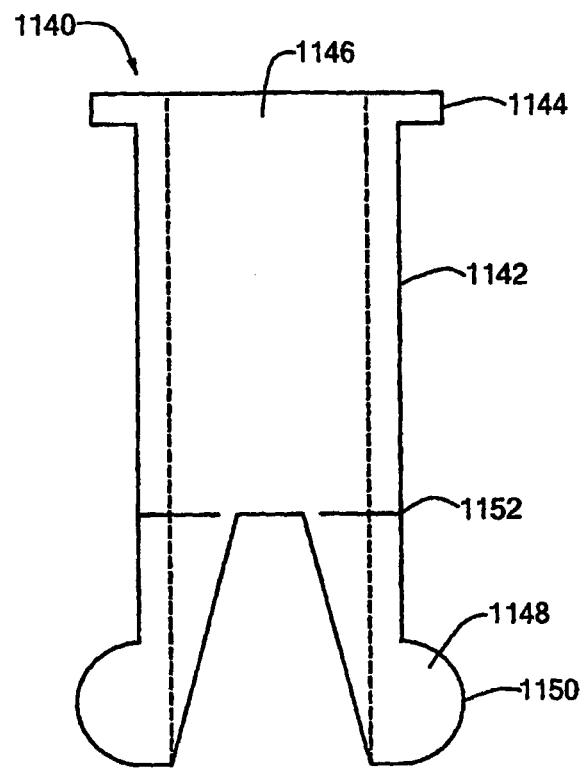
FIG. 11
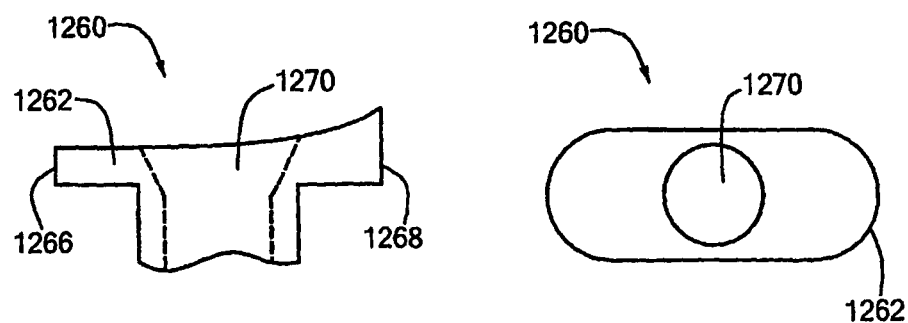
FIG. 12A  FIG. 12B

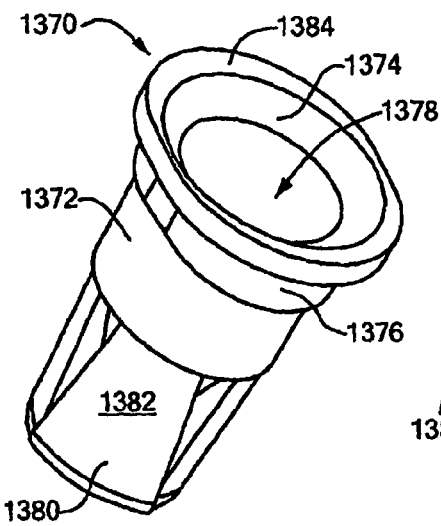
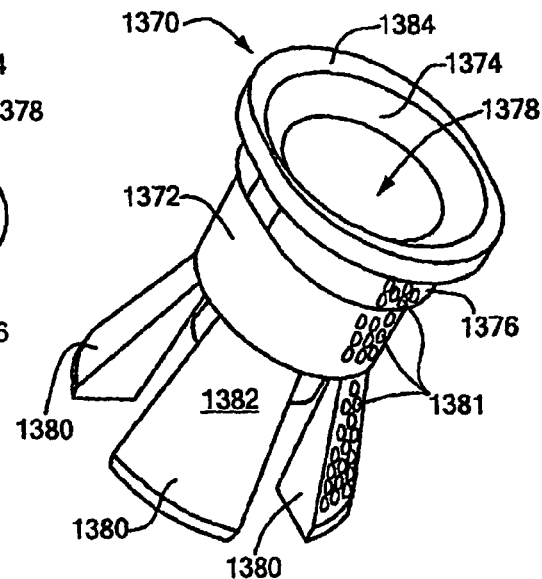
FIG. 13A
FIG. 13B
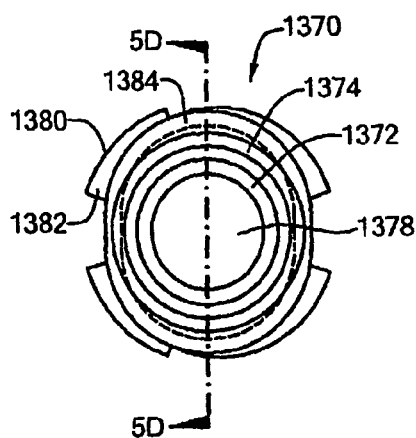
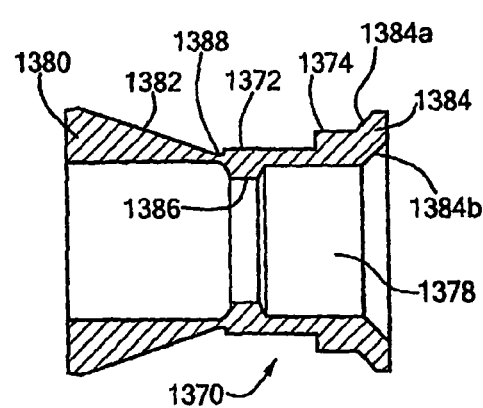
FIG. 13C
FIG. 13D

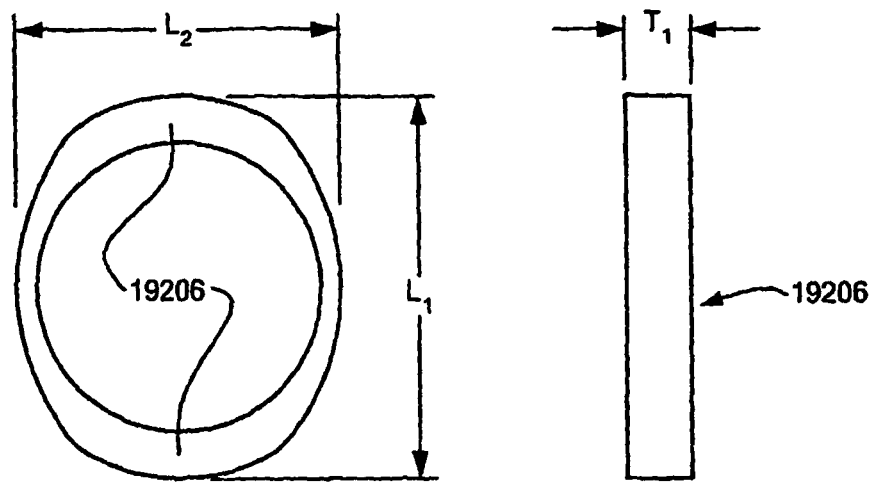
FIG. 19E    FIG. 19F
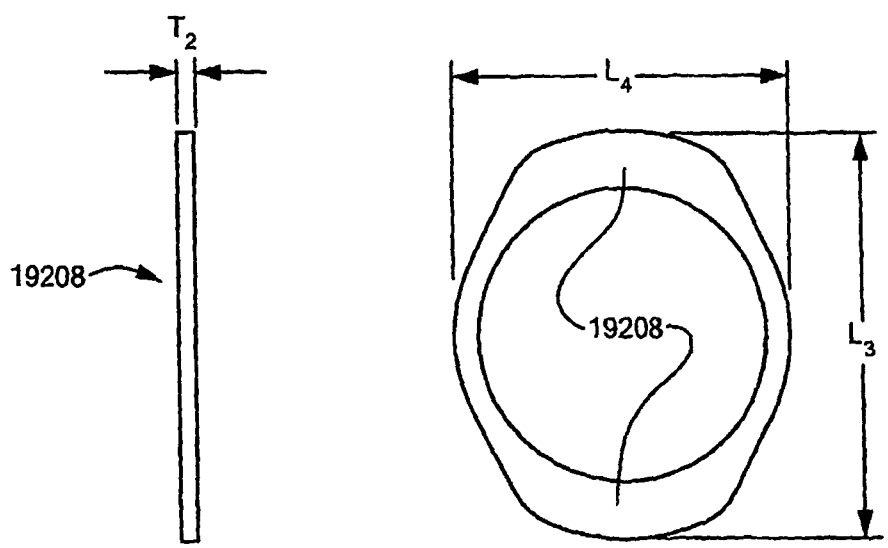
FIG. 19G    FIG. 19D

APPARATUS FOR SECURING AN IMPLANTABLE OBJECT TO BONE

CROSS REFERENCE TO RELATED APPLICATIONS

This application claims the benefit of PCT Application No. PCT/US2004/014640 filed on May 10, 2004 which claims the benefit of provisional patent application Ser. No. 60/468,829 filed May 8, 2003, the disclosure of which is incorporated herein by reference and this application is a continuation-in-part (CIP) of patent application Ser. No. 10/246,304 filed on Sep. 18, 2002, which claims the benefit of provisional patent application Ser. Nos. 60/323,347 filed on Sep. 18, 2001, 60/347,212 filed on Jan. 10, 2002, and 60/374,534 filed on Apr. 22, 2002 the disclosures of which are each incorporated herein by reference.

STATEMENT REGARDING FEDERALLY SPONSORED RESEARCH

Not Applicable

FIELD OF THE INVENTION

The present invention relates generally to surgical fasteners. More particularly, the present invention relates to a mounting or anchoring device for use with a screw or bone being fastened to a bone or other body structure.

BACKGROUND OF THE INVENTION

As is known in the art, fasteners such as screws or pins are commonly used to secure or mate fractured bone sections. For example, a bone fracture can be held together during the healing process by means of a fastener such as a surgical screw. Such screws and the manner in which the screws are selected for use are known.

The process of inserting the screw involves first properly aligning the bone regions to be secured by the screw. A hole is then drilled through the bone regions. After the hole is drilled, the hole is tapped. The diameter of the screw to use, the size of the hole to drill, and the size of the tap are selected in accordance with a variety of well-known factors including but not limited to the size of the bone as is generally known by those of ordinary skill in the art.

One problem that arises, however, is that as a screw is being inserted into the hole in the bone, the screw hole may become stripped and the screw no longer obtains adequate purchase in the bone. A screw having inadequate purchase is sometimes referred to as a "spinner." Reasons for this failure of fixation include poor bone quality, over-tightening of the screw and an error in the drilling or tapping of the screw hole (e.g. the tap itself cuts a new hole because the tap does not enter the drilled hole at the proper angle, the drill does not produce a straight hole, etc. . . . ). Other problems can also occur. For example, while the hole is being drilled, the fracture may shift which results in the existing hole being in a sub-optimal position.

One technique for addressing such a problems is to inject a bone cement (e.g. methylmethacrylate) into the screw hole and re-insert the screw while the bone cement hardens. This is a cumbersome and time-consuming process and also runs the risk of having the bone cement travel into the fracture site and impeding bony union. As a result of these and other risks, this technique is seldom utilized.

Another technique, which is more frequently utilized than the bone cement technique, is to attempt to drill another hole in a new position. However, this is not always possible due to a variety of factors including but not limited to the type and location of the bone fracture being repaired as well as the condition (e.g. quality) of the bone being repaired. A new drill hole may now create too large a drill hole or a drill hole with too thin a wall adjacent to the previous hole and again compromise or eliminate effective screw purchase. It is sometimes necessary to simply accept less than optimal fixation, or in some cases even substandard fixation, and possibly alter the post-operative rehabilitation plan. This may entail delaying weight-bearing or early motion and possibly compromising the patient's outcome.

In some cases, bone plates are used to obtain fixation and are commonly secured to the bone by screws. The use of bone plates can improve stability of the fractured bone gained by applying compression across the fracture site. Use of bone plates, however, can also make it more difficult to deal with spinners since the holes drilled in the bones must also match the locations of pre-drilled holes in the bone plates.

Another problem that arises is that osteoporotic bone or bone with abnormally thinned cortices due to failed fixation or previous infection may not allow lasting screw purchase in the bone. Thus, a surgical screw may first appear to have adequate purchase but due to bone or other conditions, the screw fails to maintain adequate screw purchase in the bone over a requisite period of time. Once the screw loosens in the bone, stability of the fractured bone gained by applying compression across the fracture site is quickly lost. A number of techniques for securing screws in a bone plate are described in U.S. Pat. Nos. 5,976,141 and 4,484,570.

SUMMARY OF THE INVENTION

In accordance with the present invention, a Fixation Augmentation Device (FAD) includes a tubular body or sleeve having a collar disposed on a first end thereof. The sleeve is provided having an outside diameter selected such that the sleeve fits into a hole drilled in a bone. The collar at the first or proximal end of the sleeve prevents advancement of the FAD into the hole with screw insertion. With this particular arrangement, a device that allows a surgeon to quickly remove a "spinner" screw and reinsert the screw in a manner such that a screw which obtains adequate purchase is provided. Furthermore by utilizing the FAD the originally selected angle of the screw relative to the fracture is maintained. The FAD improves screw purchase by effectively restoring the appropriate sized hole for screw purchase thereby giving press fit interference fixation along the inner walls of the drill hole. The outer walls of the FAD can be ribbed, threaded, fretted or otherwise textured to enhance this fixation. In addition, the shape of the outer wall of the interference portion allows the FAD to hook over the bone cortices to further enhance fixation. The FAD thus takes advantage of the tubular aspect of the bone in order to secure fixation within the bone and outside the bone. The FAD is designed to allow the screw to obtain secure fixation to the bone in the situations where a screw has inadequate purchase. The FAD is a relatively simple device which is relatively easy and inexpensive to manufacture and to use. Furthermore, the FAD adds no significant operative time to install.

In one embodiment, the FAD can be used with a bone plate. In such an embodiment, the collar portion of the FAD is provided having a size and shape which allows the sleeve portion of the FAD to be inserted into a hole in a bone through a bone plate. Thus, when the FAD is used in conjunction with a bone plate, the sleeve portion of the FAD fits through an opening in the bone plate and is inserted into a hole which has been drilled in a bone while the collar portion of the FAD fits through the opening in the bone plate but does not fit within the hole in the bone. The collar portion of the FAD can be provided having a shape which allows insertion of the FAD through the opening in the plate but which prevents rotation of the FAD during screw insertion. For example, in the case where the opening in the bone plate is provided having a round shape, the collar portion of the FAD can be provided having an oval shape. In this case, the edges of the collar would make interfering contact with the walls of the plate which define the hole to thereby prevent rotation of the FAD. This would not be accomplished with a round collar. Small fins beneath the collar can also help to accomplish this task. The tapered fins are directed radially just beneath the collar portion and cut into the proximal cortical edge. When a rotational force is applied during screw insertion these radial fins in the FAD provide a de-rotation mechanism and facilitate the passage of the screw.

In one embodiment, the sleeve portion of the FAD is tapered and the walls of the sleeve are provided having a slot provided therein. The slots extend through the entire thickness of the sleeve. The slot may be incorporated on only one sidewall of the device, or may extend through the device, thus being incorporated into the sidewall in two places. As a screw is inserted into the FAD, the slot in the sleeve portion of the FAD allows the sleeve portion of the FAD to expand thus pressing the walls of the sleeve into the bone on the inner walls of the drill hole.

In another embodiment, the FAD includes a flange at the distal end of the sleeve (i.e. at the opposite end of the sleeve from the collar). The sleeve portion of the FAD is tapered and the walls have a slot provided therein. The slots extend through the entire thickness of the sleeve. The flange portion at the distal end of the FAD hooks over the far side of the distal cortex as the screw is seated. This is accomplished by the expansion of the sleeve due to the screw entering the sleeve. The expansion can be enhanced by filling a portion of the distal end of each inner surface of the sleeve such the outer surface of the distal end of the screw pushes against the filled inner surface at the distal end of the sleeve. As the screw passes from the hollow portion of the sleeve into the filled distal end portion of the sleeve it abuts the solid inner wall which causes further expansion of the distal end and also prevents the flange from collapsing when pullout stress is applied. This approach further increases pullout strength of the FAD.

In accordance with a further aspect of the present invention, a bone fixation augmentation device, for use in a bone having a hole provided therein, includes a first collar portion adapted to mate to a first surface of a bone, an interference region projecting from the first collar portion and having a length and a width adapted to produce an interference fit between a fastener inserted in the hole and a hole wall surface. With this particular arrangement, a device for improving the purchase of a screw is provided. In one embodiment, the first collar region is disposed at a first end of the interference region and is disposed on the surface of the bone at a first end of the hole to secure the interference region in a desired location within the hole. A second, opposite end of the interference region has a second collar portion coupled thereto. The second collar portion is adapted to mate to the surface of the bone at a second, opposite end of the hole. The second collar region secures the interference region of the FAD in the hole and increases pullout strength of the FAD. In another embodiment, the FAD includes an anti-rotation structure which prevents the FAD from rotating within the hole in the bone. The anti-rotation structure can be provided as part of the first or second collars or as part of the interference region.

In still another embodiment, the interference region is provided having one or more slots therein to allow expansion of wall which comprise the interference region in response to a screw passing through the interference region.

In still another embodiment, the interference region is provided having ridges or teeth on an outer surface thereof and one or more slots therein. The slot(s) allow expansion of walls which comprise the interference region in response to a screw passing through the interference region and the ridges help secure the FAD within the bone hole.

In still another embodiment, the interference region is provided having threads on an internal surface thereof. The threads mate with screws to be inserted within the FAD.

In still another embodiment, the interference region includes wings in a portion thereof which expand in response to a screw passing through the interference region and which secure the FAD within the bone hole.

In still another embodiment, the interference region includes wings in an end portion thereof which expand in response to a screw passing through the interference region such that when the wings are deployed, the wings engage an outer surface of the bone and increase the pull force required to remove the FAD from the bone hole.

In yet another embodiment, the interference region is provided having portions thereof such that the interference region corresponds to a spring-like or clip-like structure. The interference region can also be provided having threads which mate with screws to be inserted within the FAD.

In accordance with the present invention, a Fixation Augmentation Device (FAD) includes a tubular body or sleeve having a collar disposed on a first (proximal) end and a plurality of expandable flanges disposed about a second (distal) end. The FAD allows a screw to obtain secure fixation to a bone in the situations where a screw or other securement device may have inadequate purchase. The FAD adds no significant operative time to install.

In accordance with a further aspect of the present invention, a Fixation Augmentation Device (FAD) includes a tubular body or sleeve having a collar disposed on a first end thereof. The sleeve is provided having an outside diameter selected such that the sleeve fits into a hole drilled in a bone. The collar at the first or proximal end of the sleeve prevents advancement of the FAD into the hole with screw insertion. The sleeve includes a thread for receiving a screw. The sleeve includes one or more flanges extending a predetermined distance from a distal end of the sleeve. The portions of the sleeve defined by the slots are referred to as flanges. The flanges are displaceable at the point where the flange joins the sleeve. The flanges are displaced from a closed position to an open position by insertion of the screw. In use the FAD (with the flanges in a closed position) is inserted into the hole drilled into the bone. Once the FAD has been positioned within the hole, a screw is inserted into the FAD. As the screw is inserted into the sleeve of the FAD, the screw displaces the flanges into an open position that provides an interference fixation of the FAD within the hole.

The FAD is designed to allow the screw to obtain secure fixation to the bone in the situations where a screw has inadequate purchase. The FAD is also removable by removing the screw and pulling the FAD out of the hole. The flanges are collapsible back to the closed position thereby allowing the FAD to be readily removed. The FAD adds no significant operative time to install.

In one embodiment, the FAD is used with a bone plate. In such an embodiment, the collar portion of the FAD is provided having a size and shape that allows the sleeve portion of the FAD to be inserted into a hole in a bone through a bone plate. Thus, when the FAD is used in conjunction with a bone plate, the sleeve portion of the FAD fits through an opening in the bone plate and is inserted into a hole which has been drilled in a bone while the collar portion of the FAD fits through the opening in the bone plate but does not fit within the hole in the bone. The collar portion of the FAD can be provided having a shape which allows insertion of the FAD through the opening in the plate but which prevents rotation of the FAD during screw insertion. For example, in the case where the opening in the bone plate is provided having an oval shape, the collar portion of the FAD can be provided having an oval shape. In this case, the edges of the collar would make interfering contact with the walls of the plate that define the hole to thereby prevent rotation of the FAD. This would not be accomplished with a round collar.

In another embodiment, the FAD is again used with a bone plate however, this arrangement is different than the one described above. In this embodiment, the FAD is inserted into the bone and the bone plate is placed on top of the FAD. The hole in the bone plate is aligned with the hole of the FAD, and a screw is inserted through the hole in the bone plate and into the FAD to securely attach the bone plate to the FAD wile also securely affixing the FAD within the hole in the bone.

In yet another embodiment, a locking plate is used in combination with a FAD. The locking plate features a tapered threaded hole which receives a FAD provided with external threads which mate with the threads of the hole. The FAD may be configured such that a fully inserted FAD has it's top surface aligned with a top surface of the locking plate. In an alternate embodiment the FAD may be configured such that a fully inserted FAD has it's top surface recessed below the top surface of the locking plate. In still another embodiment, the FAD could be configured to a locking plate with a straight threaded hole as well as the tapered hole mentioned above.

In yet another embodiment the FAD is provided with an external thread for securing the FAD within a bone plate and is further provided with a slot in the inner surface of the collar. The slot accepts a flat screw driver blade and can be used to remove the FAD from a bone plate.

In still a further embodiment the FAD is integral with a bone plate. The device could include multiple FAD portions, all integrated with the bone plate into a single device.

BRIEF DESCRIPTION OF THE DRAWINGS

The invention will be more fully understood from the following detailed description taken in conjunction with the accompanying drawings, in which:

FIG. 1A is a diagram of a first embodiment of a FAD;
FIG. 1B is a cross-sectional view of the FAD of FIG. 1A;
FIG. 1C is a top view of the FAD of FIG. 1A;
FIG. 7A is a side view of a seventh embodiment of a FAD;
FIG. 7B is a side view of the FAD of FIG. 7A with a screw inserted therein;

FIG. 8 is a diagram showing a tool used for insertion of a FAD into a bone;
FIG. 9A is an isometric view of the FAD of the present invention in a closed position;
FIG. 9B is an isometric view of the FAD of FIG. 9A in an open position;
FIG. 9C is a side view of the FAD of FIG. 9B;
FIG. 9D is a cross-sectional side view of the FAD of FIG. 9B taken across lines 9D-9D of FIG. 9B;
FIG. 9E is a top view of the FAD of FIG. 9B;
FIG. 9F is a bottom view of the FAD of FIG. 9B;
FIG. 10 is a cross-sectional side view of a FAD having threads extending there through;
FIG. 11 is a side view of another embodiment of a FAD;
FIG. 12A is a side view of a collar having a tapered upper surface;
FIG. 12B is a top view of the FAD of FIG. 12A;
FIG. 13A is an isometric view of another embodiment of a FAD, wherein the FAD is shown in a closed position;
FIG. 13B is an isometric view of the FAD of FIG. 13A in an open position;
FIG. 13C is a top view of the FAD of FIG. 13B;
FIG. 13D is a cross-sectional side view of the FAD of FIG. 13B taken along lines 13D-13D in FIG. 13C.

DETAILED DESCRIPTION OF THE INVENTION

Figure 3B:
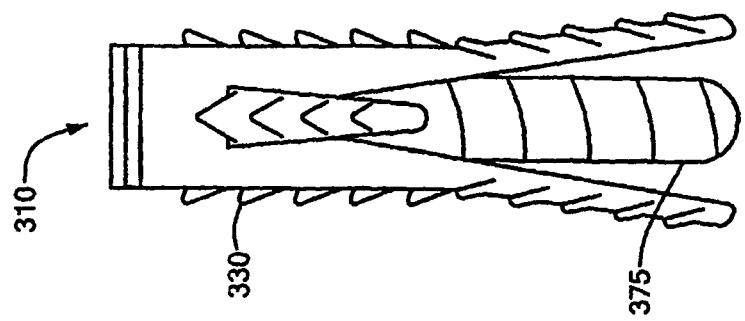
FIG. 3B is a side view of the FAD of FIG. 3A.

In accordance with the present invention, a Fixation Augmentation Device (FAD) includes a tubular body or sleeve having a collar disposed on a first end thereof. The sleeve is provided having an outside diameter selected such that the sleeve fits into a hole drilled in a bone. The collar at the first or proximal end of the sleeve prevents advancement of the FAD into the hole with screw insertion. With this particular arrangement, a device that allows a surgeon to quickly remove a "spinner" screw and reinsert the screw in a manner such that a screw which obtains adequate purchase is provided.

The FAD allows a surgeon to quickly remove a "spinner" screw and reinsert the screw in a manner such that the screw obtains adequate purchase is provided. Furthermore by utilizing the FAD the originally selected angle of the screw relative to the fracture is maintained. The FAD improves screw purchase by effectively restoring the appropriate sized hole for screw purchase thereby giving press fit interference fixation along the inner walls of the drill hole. The shape of the walls of the FAD further enhance fixation by hooking over one or more cortices of the bones after screw insertion. The FAD is designed to allow the screw to obtain secure fixation to the bone in the situations where a screw has inadequate purchase. The FAD is a relatively simple device which is relatively easy and inexpensive to manufacture and to use. Furthermore, the FAD adds no significant operative time to install.

Referring now to FIGS. 1A-1C, a bone Fixation Augmentation Device (FAD) 10 includes a tubular body or sleeve 10 corresponding to an interference region. The sleeve 10 has a collar 20 disposed on a first end thereof. The sleeve 10 is provided having an outside diameter selected such that the sleeve fits into a hole drilled in a bone. The collar at the first or proximal end of the sleeve prevents advancement of the FAD into the hole with screw insertion. A first interference region 40 is provided as part of the sleeve 20. Upon insertion of a screw 70 into core 30 of the sleeve 20, the first interference region (flange) 40 expands into the hollow part 90 of the bone, providing secure fixation of the FAD to the inner cortex portions 80 of the bone. The angled sidewalls of the interference region and the flange are provided such that the FAD may be removed from the hole in the bone if desired. Removal of the screw allows the flange sidewalls and interference region sidewalls to collapse such that the FAD can be removed. A flange 50 is disposed on a second end of the sleeve 20. Upon insertion of screw 70 into core 30 of the sleeve 20, the flange 50 expands along the outer cortex 80 of the bone, providing secure fixation of the FAD to the outer cortex portion 80 of the bone. The interference region and flange can be provided having one or more slots 60 therein to allow expansion of the wall which comprises the interference region and flange in response to a screw passing through the interference region. The slots extend through the entire thickness of the sleeve. As a screw is inserted into the FAD, the slot in the sleeve portion of the FAD allows the sleeve portion of the FAD to expand thus pressing the walls of the sleeve into the bone on the inner walls of the drill hole.

The expansion of the flange portion of the sleeve can be enhanced by filling a portion of the distal end of each inner surface of the sleeve such the outer surface of the distal end of the screw pushes against the filled inner surface at the distal end of the sleeve. As the screw passes from the hollow portion of the sleeve into the filled distal-end portion of the sleeve it abuts the solid inner wall which causes further expansion of the distal end and also prevents the flange from collapsing when pullout stress is applied. This approach further increases pullout strength of the FAD.

Figure 2:
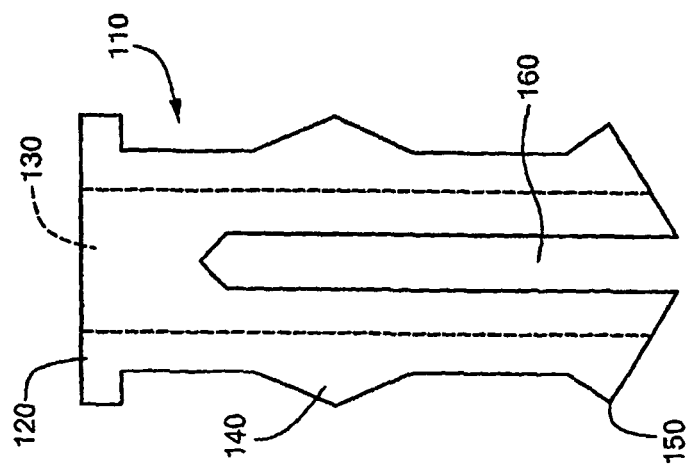
FIG. 2 is a diagram of a second embodiment of a FAD.

A second embodiment of a FAD 110, is shown in FIG. 2. The FAD 110 has a similar structure as FAD 10. FAD 110 includes a collar 120, a core 130, an interference region 140, a flange portion 150 and a slot 160. Operation of FAD 110 is similar to the operation of FAD 10 described above. FAD 110 clips into place in a bone hole. Slot 160 allows for the ends of the FAD to adequately clip into place.

Figure 3A:
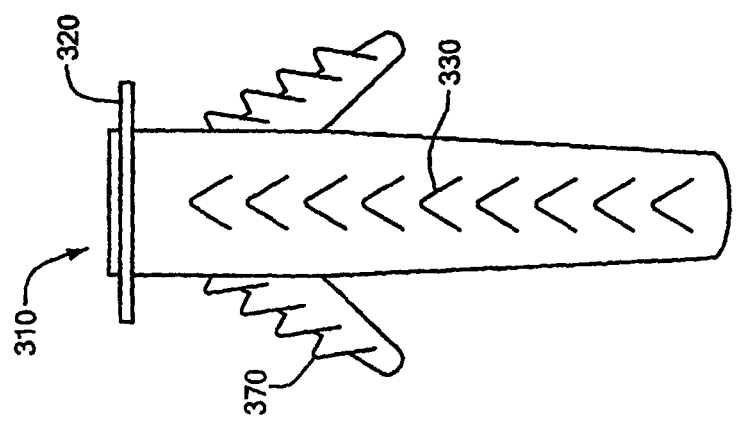
FIG. 3A is a diagram of a third embodiment of a FAD.

Referring now to FIGS. 3A-B, another embodiment 310 of a FAD is shown. In this embodiment the interference region is provided having a plurality of ridges or teeth 330 on an outer surface thereof. The ridges 330 help secure the FAD within the bone hole. FAD 310 further includes wings 370 in the interference region which expand in response to a screw passing through the interference region and which secure the FAD within the bone hole. The outer walls of the FAD 310 can be ribbed, threaded or fretted to enhance the fixation of the device within the bone hole. Further the outer surface of the collar can also be ribbed, threaded or fretted to enhance the fixation of the device. As shown in to FIG. 3B, the interference region includes wings 375 in an end portion thereof which expand in response to a screw passing through the interference region such that when the wings are deployed, the wings engage an outer surface of the bone and increase the pull force required to remove the FAD 310 from the bone hole.

Figure 4A:
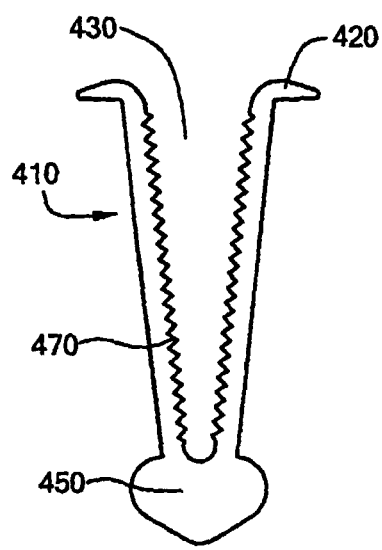
FIG. 4A is a side view of a fourth embodiment of a FAD.
Figure 4B:
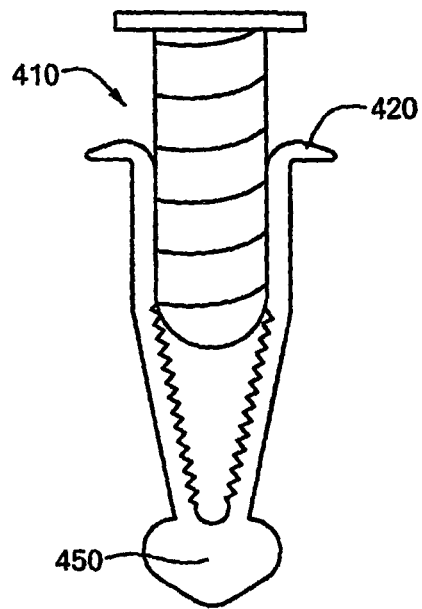
FIG. 4B is a cross-sectional view of the FAD of FIG. 4A with a screw inserted therein.

Referring now to FIGS. 4A-B, an embodiment of another Fad 410 is shown. This embodiment uses a "clip" style body having an aperture 430 disposed most of the way through. The aperture 430 includes a threaded region 470 along an inner wall. The threaded region helps secure a screw in the body to provide an expanding wedge type fit within the bone hole. A collar region 420 is disposed at a first end of the body and is disposed on the surface of the bone at a first end of the hole to secure the body in a desired location within the hole. A second, opposite end of the interference region has a second collar portion 450 coupled thereto. The second collar portion is adapted to mate to the surface of the bone at a second, opposite end of the hole. The second collar region helps secure the FAD 410 in the hole and increases pullout strength of the FAD.

Figure 5:
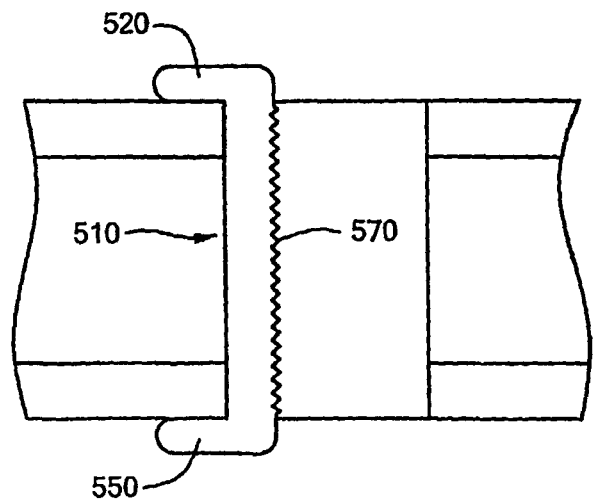
FIG. 5 is a side view of a fifth embodiment of a FAD.

FIG. 5 shows a FAD useful for smaller holes. FAD 510 is are provided from a single member which fills only a portion of a hole in a bone. FAD 510 includes collar 520 and 550 on opposing ends thereof. The FAD 510 may also have threads 570 provided therein. This FAD 510 function in a similar manner as those described above with respect to FIGS. 4A-B.

Figure 6A:
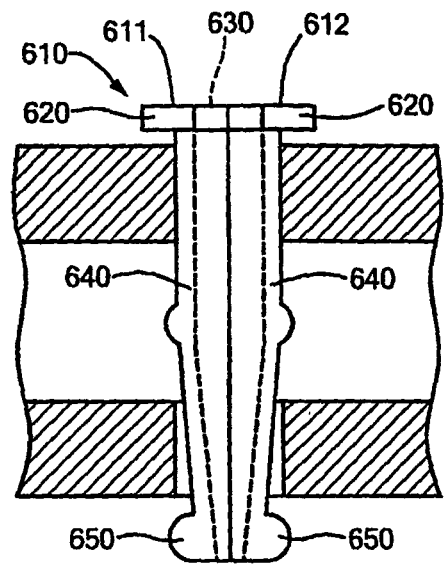
FIG. 6A is a side view of a sixth embodiment of a FAD.
Figure 6B:
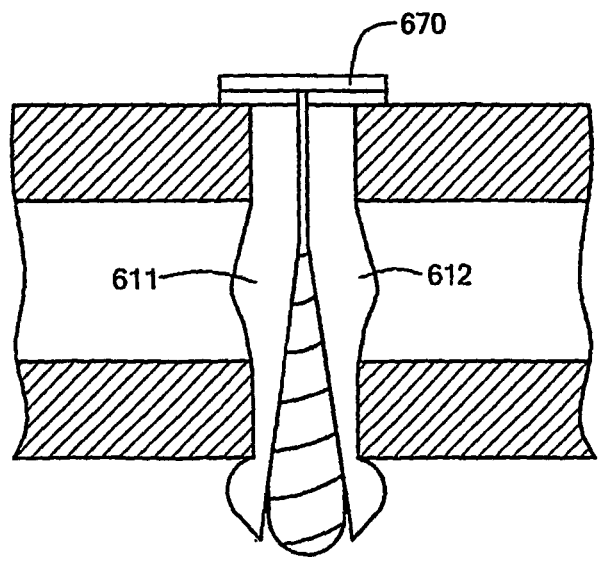
FIG. 6B is a side view of the FAD of FIG. 6A with a screw inserted therein.

Referring now to FIGS. 6A-B, a "split" FAD 610 is shown. This FAD 610 is comprised of two complimentary pieces 611 and 612, each piece representing approximately half of the FAD. Alternately, the Fad can be comprised as a single piece which splits into two pieces upon insertion of screw 670. Each piece includes a respective collar portion 620, interference region 640 and flange region 650. The FAD is inserted into the bone hole, and upon insertion of a screw 670 the pieces 611 and 612 are separated and provide interference fit of the screw within the bone hole. The operation of the FAD 610 in other respects is similar to that of FIGS. 1A-C described above.

Referring now to FIGS. 7A-B, a telescoping FAD 710 is shown. This FAD 710 includes a distal portion 730 and a proximal portion 740. The two portions 730 and 740 are provided having geometries such that the portions can telescope (e.g. the distal portion can move into the proximal portion). Screw insertion pulls the distal portion 730 into the proximal portion 740 causing expansion of the proximal portion. Flared out edges of the proximal portions provide the FAD having improved fixation at the proximal cortex on the intramedullary side. A slot 760 expands upon insertion of screw 770 and flange 750 provides for secure engagement of the FAD within the bone hole. As shown in FIG. 7A, prior to engagement of the FAD 710, a fracture line 790 of a bone is uncompressed. In FIG. 7B, after insertion and engagement of the FAD 710, the fracture line 790 is compressed.

Referring now to FIG. 8, an apparatus 810 for holding a FAD during a FAD or screw insertion process includes a handle 820 and a body 830 coupled to the handle. The body 830 is adapted to hold a FAD while the FAD is inserted in a bone hole. The body holds the FAD in a manner which still allows insertion of a screw into the FAD. In one embodiment, the body is provided having a hole therein through which the screw can be inserted into the FAD. The apparatus can also include a FAD anti-rotation structure which minimizes FAD or even prevents FAD rotation which can occur when a screw is inserted into the FAD.

The procedure for FAD installation will now be described. Once the surgeon realizes that he/she has either sub-optimal fixation or a sub-optimally positioned drill hole, the hole is over drilled utilizing an appropriately sized larger drill (i.e. 4.0 mm drill for a 3.5 mm cortical screw). The FAD length corresponding to the selected screw length is then placed onto the FAD inserter and placed securely into the drill hole. Now the screw is inserted into the FAD. As the screw advances the walls of the FAD expand giving interference fixation to the bone along the inner walls of the drill hole. In addition, the expansion allows the FAD to hook over the inner side of the cortex with the flange at the central portion of the interference region. The FAD expands even further at the distal end and deploys the distal flange over the edge of the distal cortex, increasing the fixation to the bone. Once the screw is fully seated, secure fixation is once again established.

In one embodiment, the FAD can be used with a bone plate. In such an embodiment, the collar portion of the FAD is provided having a size and shape which allows the sleeve portion of the FAD to be inserted into a hole in a bone through a bone plate. Thus, when the FAD is used in conjunction with a bone plate, the sleeve portion of the FAD fits through an opening in the bone plate and is inserted into a hole which has been drilled in a bone while the collar portion of the FAD fits through the opening in the bone plate but does not fit within the hole in the bone. The collar portion of the FAD can be provided having a shape which allows insertion of the FAD through the opening in the plate but which prevents rotation of the FAD during screw insertion. For example, in the case where the opening in the bone plate is provided having a round shape, the collar portion of the FAD can be provided having an oval shape. In this case, the edges of the collar would make interfering contact with the walls of the plate which define the hole to thereby prevent rotation of the FAD. This would not be accomplished with a round collar. Small fins beneath the collar also help to accomplish this task.

Although, in the above examples the FAD collar portion is provided having an oval shape, it should be appreciated that any shape, including but not limited to rectangular, triangular, polygonal or even irregular shapes can be used. The particular shape with which to provide the collar portion of the FAD depends upon a variety of factors including but not limited to the size and shape of the opening in the bone plate, the size of the FAD, the strength required to withstand forces applied to the collar portion of the FAD and the materials from which the bone plate and FAD are manufactured.

Figure 9G:
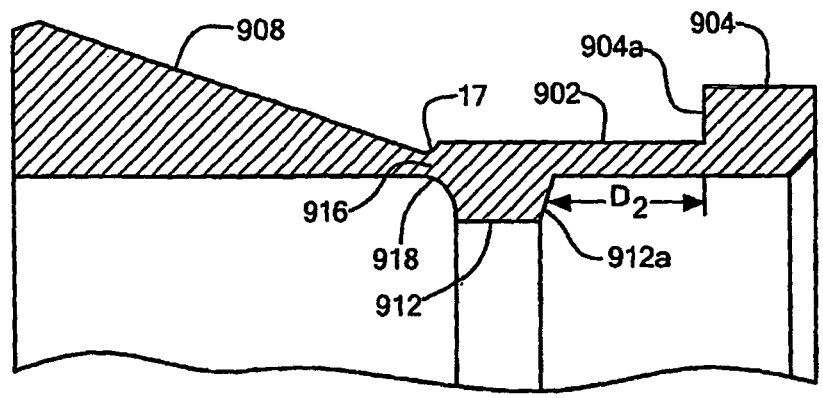
FIG. 9G is an enlarged view of a portion of the FAD shown in FIG. 9D taken along lines 9G-9G.

Referring now to FIGS. 9A-9G in which like elements are provided having like referable designations throughout the several views, a first FAD 901 includes a tubular body or sleeve portion 902. The sleeve 902 has a collar 904 disposed on a first end thereof. Collar 904 preferably has a generally oval shape that prevents rotation of the device when inserted into a bone plate or to allow a surface for a tool to use during the insertion of the device 901 or during insertion of a screw into the device 1. The sleeve 902 is provided having an outside diameter $D_1$ (FIG. 9D) selected such that the sleeve fits into a hole drilled in a bone. The collar 904 at the first or proximal end of the sleeve 902 prevents advancement of the FAD 901 into the hole with screw insertion. The second end of tube 902 has one or more flanges 908 coupled thereto. In the exemplary embodiment of FIGS. 9A-9G, device 901 is shown having four flanges 908. Those of ordinary skill in the art will appreciate of course that device 901 could include fewer or more than four flanges 908. Surfaces 910 (FIG. 9B) of the flanges 908 are angled to allow the flanges to be placed in both an open position (FIG. 9B) and a closed position (FIG. 9A).

Upon insertion of a screw into core 906 of the sleeve 902, flanges 908 expand (as shown in FIG. 9B), providing secure fixation of the FAD 901 to the bone. The angled sidewalls 910 of the flanges 908 also allow the FAD 901 to be removed from the hole in the bone if desired. The screw is preferably withdrawn from the FAD 901 by an amount which allows the flanges 908 to collapse by an amount which allows the FAD 901 to be removed. This can be accomplished by partially unscrewing the screw from the FAD by an amount which allows the flanges to close by an amount sufficient to allow the FAD to be withdrawn from the bone. This amount may be a full collapse of the flanges back into the closed position. Or, it may be a partial collapse of the flanges to less than the fully closed position by an amount which still allows the FAD to be removed. Thus, in this case, the screw is not totally removed from the FAD. In some cases, however, it may be desirable or necessary to fully removed the screw from the FAD to allow the FAD to be removed.

Referring now in particular to FIG. 9D additional features of the FAD 901 are shown. The FAD includes a thread 912 for receiving a screw therein. Thread 912 is preferably located at the distal end of body 902 and proximate flanges 908. In one embodiment, the thread 912 is located to account for a "runin" region of a screw.

As shown in FIG. 9G, a first surface 912a of thread 912 is spaced by a predetermined distance $D_2$ from a first surface 904a of the collar 904 and a second surface 912b of thread 912 is spaced by a predetermined distance $D_3$ from the first surface 904a of the collar 904. In one embodiment, for an overall device length of about 0.294 inches, the distances D1 and D2 correspond to about 0.090 inches and about 0.137 inches respectively, flange lengths $L_2$ (FIG. 9C) correspond to about 157 inches and slot openings $S_1$ (FIG. 9C) are about 0.039 inches and $S_2$ (FIG. 9C) about 0.080 inches. Other lengths, diameters and slot sizes may, of course, also be used. The particular length and overall upper (i.e. collar) and lower (i.e. flange) diameters to be use in any particular application will be determined in accordance with a variety of factors including but not limited to the length and diameter of screws being inserted. Likewise, the particular size of slot openings to be used in any application will be determined in accordance with a variety of factors including but not limited to the length and overall diameter of the FAD as well as the length and diameter of screws being inserted into the FAD. Also, the FAD 901 is provided having a lower flange diameter $D_2$ (FIG. 9F) in the range of about 0.254 inches and a flange having a length $F_1$ between flat section of about 0.165 inches and a radius R of about 0.0825 inches and a length $L_3$ of about 0.207 inches In another embodiment, for an overall device length of about 0.304 inches, the distances $D_2$ and $D_3$ correspond to about 0.104 inches and about 0.147 inches respectively.

In still another embodiment, for an overall device length L of about 0.508 inches, the distances $D_1$, $D_2$, $D_3$ and $D_4$ (FIG. 9F) correspond to about 0.181 inches, 0.144 inches, 0.274 inches and about 0.312 inches respectively; and the distances L2 and L3 are about 0.234 and about 0.300, respectively.

Also shown in FIG. 9G is a junction area 916 where a flange 908 joins and emanates from body 902. Junction area 916 serves as a hinge or pivot point for the flanges 908. The junction area 916 is preferably sized to allow the flange 908 to be displaced from a closed position to an open position, and also to allow the flange 908 to be returned to the closed position from the open position. If this area is too thick, a relatively large amount of force will be required to cause the flange to open and thus it will be difficult to insert the screw. It will also be difficult to remove the FAD once the screw is removed. On the other hand, if the junction area is too small, there is a likelihood of the junction breaking, resulting in the device becoming unusable. The junction area 916 is preferably provided having a generally curved outer surface 917 and a generally curved inner surface 918 to reduce an occurrence of sharp bend points that could compromise the structure integrity of the junction. One exemplary junction area 916 is shown in FIG. 9G.

The flanges 908 are designed to meet several criteria. While the number of flanges 908 shown in the drawings is four, any number of flanges 908 could be used depending up on the application requirements. The size of the flanges 908 are determined such that when the flanges 8 are in the closed position (as shown in FIG. 9A) the flanges 908 can be inserted into a hole which has been prepared in the bone while still providing a sufficient interference fit within the hole after a screw is inserted within the device 901. The shape of the flanges 908 is also selected to allow sufficient interference fit when deployed (FIG. 9B), and further to allow the device 901 to be removed with minimal stress being placed on the bone.

Figure 10:
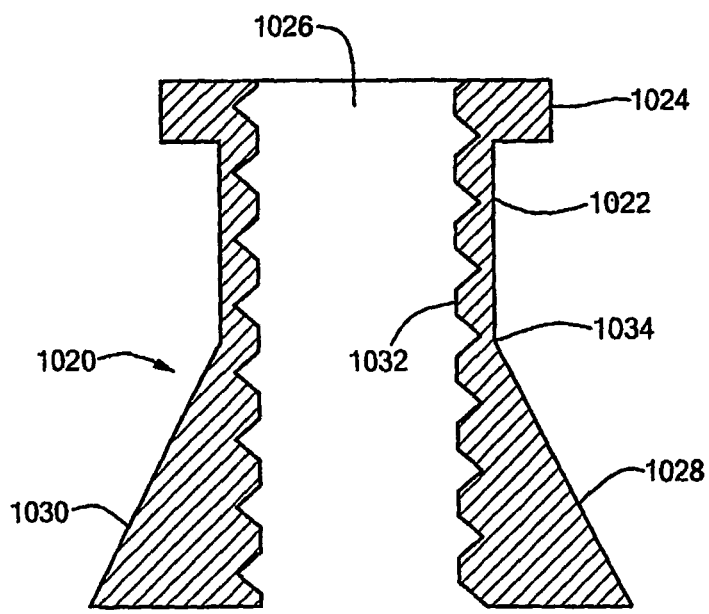

An alternate embodiment of a FAD 1020 is shown in FIG. 10. In this embodiment the FAD 1020 includes a body 1022, collar 1024, core 1026, flanges 1028 and junction points 1034 which may be similar to those described above in conjunction with FIGS. 9A-9G. FAD 20 has threads 32 extending substantially the length of the opening 1026. Thus, when a screw is inserted into FAD 1020, the screw remains in threaded engagement with the flanges 28 as they are deployed from a closed position to an open position.

Another alternate embodiment is shown in FIG. 11. In this embodiment, the FAD 1140 has a similar body 1142, collar 1144, core 1146, flanges 1148 and junction points 1152 as that of the FAD 901 described above in conjunction with FIGS. 9A-9G. The flanges 1148 in FAD 1140 have an engagement portion 1148 including a generally semi-circular shaped outer wall surface 1150. The outer wall surface 1150 provides for secure fixation of the device within a bone or plate since the semi-circular shaped ends can fit over an outer surface of the bone or plate the FAD 1140 is being affixed to.

Referring now to FIGS. 12A and 12B, a collar 1262 of FAD 1260 is shown which is preferably used with a type of bone plate known as a compression plate (CP) which may, for example, be provided as Dynamic Compression Plate. A CP has one or more holes for receiving a screw wherein the inner surface of the screw hole has a sloped surface such that as a screw is inserted, the plate compresses the bone together. Collar 1262 of FAD 60 features a sloped collar surface 1264 about core 1270 to match the sloped inner surface of a hole in the CP. The outer edge portion 1268 has a larger cross-sectional area than outer edge portion 1266, thus providing a slope region for collar 1262.

Referring now to FIGS. 13A-13D, a fourth embodiment of a FAD 1370 is shown. FAD 1370 includes a tubular body or sleeve 1372. The sleeve 1372 has a collar 1374 disposed on a first end thereof. Collar 1374 preferably has a generally oval shape that prevents rotation of the device when inserted into a bone plate or to allow a surface for a tool to use during the insertion of the device or during insertion of a screw into the device. A generally oval shoulder section 1384 is shown extending from the collar 1374. Shoulder 1384 has a tapered outer wall surface 1384a (FIG. 13D) and a tapered inner wall surface 1384b. FAD 1370 is preferably used with a bone plate, wherein the collar 1374 extends through a hole in the bone plate while shoulder 1384 extends into and engages an inner surface of the hole in the bone plate. The FAD 1370 is inserted into the bone plate hole and into the bone hole. When a screw is inserted into FAD core 1378, the FAD 1370 is securely engaged with the bone plate by way of shoulder 1384, while FAD 1370 itself is secured to the bone hole by flanges 1380.

A FAD may be provided having a bone in-growth treatment 1381 applied thereto. The bone in-growth treatment 1381 could be a coating that is applied to the FAD, such as hydroxyapatite or could be realized as a treatment which is performed on the FAD to result in a textured surface which promotes bone in-growth to aid in securing the FAD to the bone structure. The bone in-growth treatment 1381 could be applied to at least a portion of one or more flanges 1382, at least a portion of the collar 1376, at least a portion of the sleeve 1372 or a combination thereof. The use of a FAD having a bone in-growth treatment 1381 applied thereto is particularly useful in scenarios where the bone may not have a large amount of mass for a FAD to attach to or where the FAD will be used as part of a structure that may support a lot of movement or weight, for example in securing a replacement hip socket to a pelvic bone.

The sleeve 1372 is provided having an outside diameter selected such that the sleeve fits into a hole drilled in a bone. The collar at the first or proximal end of the sleeve prevents advancement of the FAD 1370 into the hole with screw insertion. Upon insertion of a screw into core 1378 of the sleeve 1372, flanges 1380 expand (as shown in FIG. 13B), providing secure fixation of the FAD 1370 to the bone. The angled sidewalls 1382 of the flanges 1380 are provided such that the FAD 1370 may be removed from the hole in the bone if desired. Removal of the screw from the FAD 1370 allows the flanges 1380 to be collapsed such that the FAD 1370 can be removed.

Referring now in particular to FIG. 13D additional features of the FAD 1370 are shown. The FAD 1370 includes a thread 86 for receiving a screw therein. Thread 1386 is preferably located at the distal end of body 1372 and proximate flanges 80. The position of the thread 1386 from the collar 1384 is selected to accommodate the run-in of the screw thread beneath the screw head and then the thread 1386 on the inner wall is preferably provided as short as possible to minimize the length of the tube portion. It could, in some applications, be desirable to lengthen the tube portion (e.g. as shown in FIG. 11) so then the thread position may not be close at all to the flange. The "run-in" length assumes use with current bone screws but conceivably a screw with a minimal, or essentially no run-in, could be used in conjunction with the FAD. Also shown in FIG. 13D is the junction area 1388 where a flange 1380 emanates from body 1372.

This junction area 1388 serves as the hinge or pivot point for the flanges 1380. The junction area is preferably sized and located relative to the flanges to allow the flanges to be displaced from a closed position to an open position, and also to allow the flanges to be returned to the closed position from the open position. Specifically, the thickness of the wall in the junction area should preferably be selected to allow the flanges 1380 to move from a closed position to an open position and then back to a closed position again if necessary. If the junction area is too thick, it will be difficult to insert the screw and to obtain the desired purchase within the bone and it will also be difficult to remove the FAD once the screw is removed. On the other hand, if the junction area is too small, there is a likelihood of the junction breaking, resulting in the device becoming unusable. The junction area 1388 is preferably provided having a generally curved outer surface and a generally curved inner surface to reduce an occurrence of sharp bend points that could compromise the junction.

The flanges 1380 are designed to meet several criteria. While the number of flanges shown in the drawings is four, any number of flanges could be used depending on the application requirements. The size of the flanges are determined such that when the flanges are in the closed position the flanges can be inserted into the drill hole while still providing a sufficient interference fit within the hole of the bone when a screw is inserted within the device. The shape of the flanges is also selected to allow sufficient interference fit when deployed, and further to allow the device to be removed with minimal stress being placed on the bone.

Figure 14A:
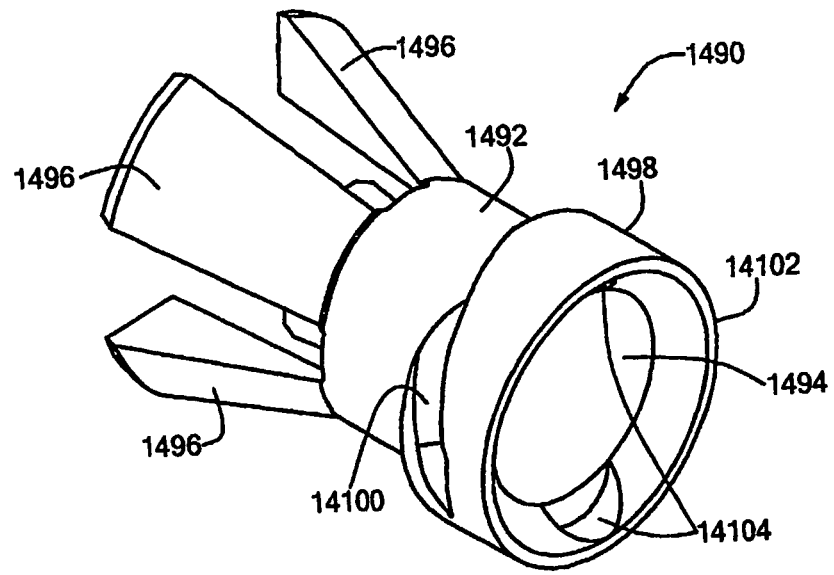
FIG. 14A is a isometric view of a further embodiment of a FAD having a collar slot.

Referring now to FIG. 14A, another embodiment of a FAD 1490 is shown. The FAD in this embodiment is similar to FAD 1370 described above in connection with FIGS. 13A-13D above and has some additional features. FAD 1490 includes a sleeve 1492, a core 1494, flanges 1496 and a collar 1498, generally similar to the FADs described above in conjunction with FIGS. 9A-13D. Collar 1498 is provided with an external thread 100 which is used to attach the FAD to a bone plate and to prevent the FAD from rotating within the bone or bone plate when a screw is inserted into the core 1494. Collar 1498 is also provided with a flat outer surface portion 14102. This flat outer surface portion 14102 provides a place for an anti-rotation device to secure the FAD while a screw is removed from core 1494. Collar 1498 further includes a slot 14104 disposed across an inner surface of the collar 1494. The slot 14104 accommodates a flat blade of a screw driver. A screw driver can be used to rotate the FAD 1490 by way of slot 14104 to unlock the FAD from the bone plate, such that the FAD 1490 could then be removed.

Figure 14B:
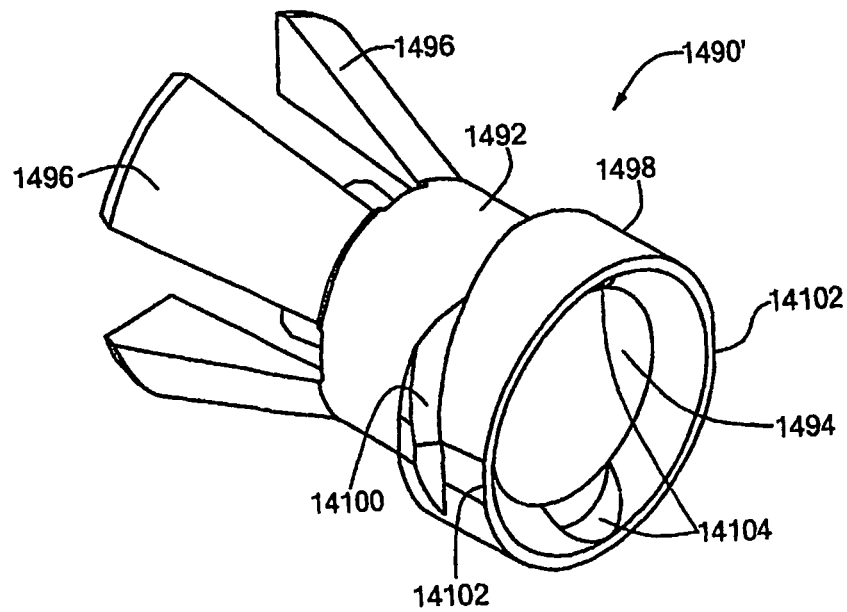
FIG. 14B is an isometric view of a second embodiment of a FAD having a collar slot.
Figure 14C:
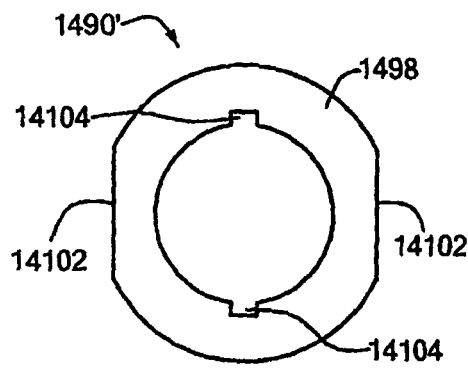
FIG. 14C is a top view of the FAD of FIG. 14B.

Referring now to FIGS. 14B and 14C, a FAD 1490' is shown. FAD 1490' is similar to Fad 1490 and includes a sleeve 1492, a core 1494, flanges 1496 and a collar 1498'. Collar 1498' is also provided with an external thread 14100 which is used to attach the FAD to a bone plate and to prevent the FAD from rotating within the bone or bone plate when a screw is inserted into core 1494. Collar 1498 further includes a slot 14104 disposed across an inner surface of the collar 1494. Collar 1498' is provided with multiple flat outer surface portions 14102. These multiple flat outer surface portions provide a place for an anti-rotation device to secure the FAD while a screw is removed from core 1494.

Figure 14D:
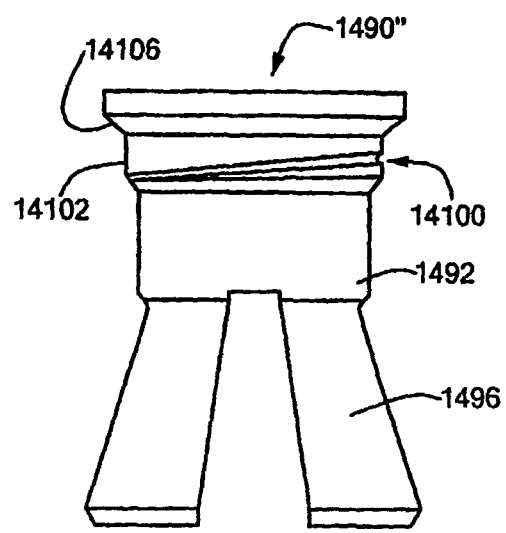
FIGS. 14D and 14E illustrate another embodiment of a FAD having a collar slot.
Figure 14E:
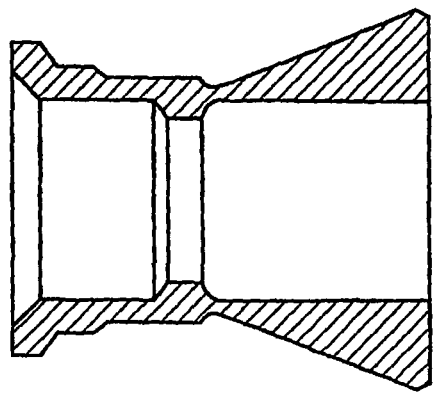

Referring now to FIGS. 14D and 14E, a FAD 1490" is shown. FAD 1490" is similar to Fad 1490 and includes a sleeve 1492, a core 1494, flanges 1496 and a collar 1498. Collar 1498 is provided with an external thread 14100 which is used to attach the FAD to a bone plate and to prevent the FAD from rotating within the bone or bone plate when a screw is inserted into core 1494. Collar 1498 further includes a slot 104 disposed across an inner surface of the collar 1494. Collar 1498 is provided with multiple flat outer surface portions 14102. These multiple flat outer surface portions provide a place for an anti-rotation device to secure the FAD while a screw is removed from core 1494. In this embodiment the collar includes a tapered outer surface portion 14106. The tapered outer surface portion 14106 is used for mating with a bone plate having a hole with a corresponding tapered or counter-sunk inner surface.

The FADs described herein are preferably comprised of stainless steel although other materials such as titanium or a bio-absorbable material having acceptable mechanical properties could be used. Also, plastics such a polymethylmethacrylate (PMMA) or other biocompatible plastics can also be used. Although in the examples provided herein the FAD collar portion is sometimes provided having a circular or oval shape, it should be appreciated that any shape, including but not limited to rectangular, triangular, polygonal or even irregular shapes can be used. The particular shape with which to provide the collar portion of the FAD depends upon a variety of factors including but not limited to the size and shape of the opening in the bone plate, the size of the FAD, the strength required to withstand forces applied to the collar portion of the FAD and the materials from which the bone plate and FAD are manufactured.

The FAD can be used with a bone plate. In such an embodiment, the collar portion of the FAD is provided having a size and shape that allows the sleeve portion of the FAD to be inserted into a hole in a bone through a bone plate. Thus, when the FAD is used in conjunction with a bone plate, the sleeve portion of the FAD fits through an opening in the bone plate and is inserted into a hole which has been drilled in a bone while the collar portion of the FAD fits through the opening in the bone plate but does not fit within the hole in the bone. The collar portion of the FAD can be provided having a shape which allows insertion of the FAD through the opening in the plate but which prevents rotation of the FAD during screw insertion. For example, in the case where the opening in the bone plate is provided having an oval shape, the collar portion of the FAD can also be provided having an oval shape. In this case, the edges of the collar would make interfering contact with the walls of the plate that define the hole to thereby prevent rotation of the FAD. This would not be accomplished with a round collar.

Figure 15:
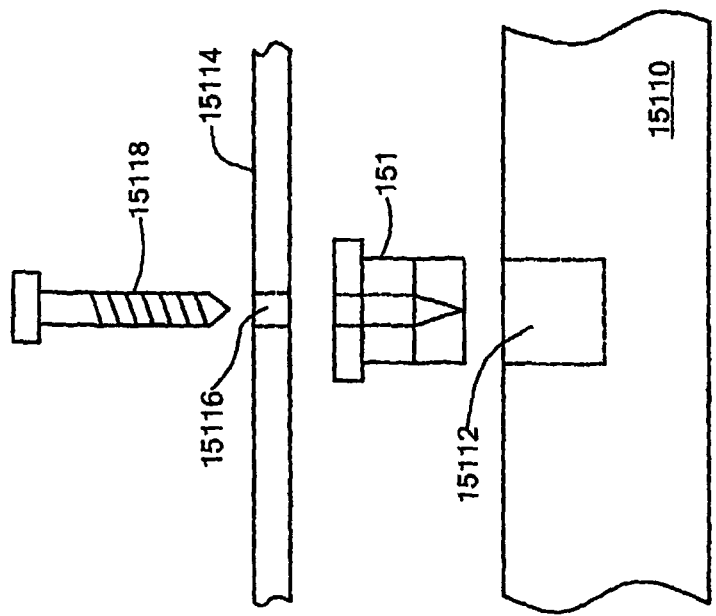
FIG. 15 is an exploded view of the FAD being used with a bone plate.

Referring now to FIG. 15, once it is required that a FAD is required (e.g. because a surgical screw fails to provided a desired or adequate purchase (or fastening strength), then one possible procedure for FAD installation includes aligning a bone plate over a bone, using existing holes in the bone plate as a guide to drill one or more holes into (and partially or fully) through the bone. With the bone plate aligned over the holes, the FAD is disposed through the hole in the bone plate and into the hole which was drilled in the bone. A screw 15118 is then inserted through the hole 15116 in the bone plate 14114 and into the FAD 901. As the screw advances, the flanges of the FAD 901 expand giving interference fixation to the bone along the inner walls of the drill hole 15112. Once the screw 15118 is fully seated, secure fixation of the bone plate 15114 to the bone 15110 is established.

Another possible procedure for FAD installation includes is described. Once a surgeon or other medical practitioner has determined that a FAD is required, a hole 15112 is drilled into bone 15110 utilizing an appropriately sized drill for the FAD 901 being used. The FAD 901 is then placed into the drill hole 15112. The bone plate 15114 is then positioned on bone 15110 such that the hole 15116 in bone plate 15114 is aligned with the hole in FAD 901. Once aligned, a screw 15118 is inserted through the hole 15116 in bone plate 15114 and into the FAD 901. As the screw advances, the flanges of the FAD 901 expand giving interference fixation to the bone along the inner walls of the drill hole 15112. Once the screw 15118 is fully seated, secure fixation of the bone plate 15114 to the bone 15110 is established.

Figure 16:
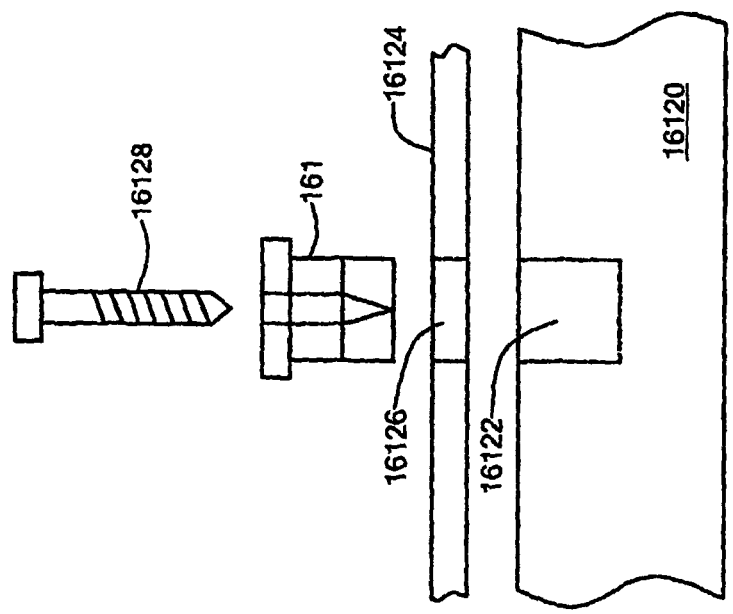
FIG. 16 is an exploded view of a second arrangement of a FAD used with a bone plate.

Referring now to FIG. 16, an alternate procedure for FAD installation is shown. Once the surgeon has determined that a FAD is required, a hole 16122 is drilled into bone 16120 utilizing an appropriately sized drill for the FAD 901 being used. The bone plate 16124 is then positioned on bone 16120 such that the hole 16126 in bone plate 16124 is aligned with the hole 16122 in the bone 16120. The FAD 901 is then placed into and extending through the hole 16126 of bone plate 16124 and into the drill hole 16122 of bone 16120. A screw 16128 is inserted into the FAD 901. As the screw advances, the flanges of the FAD 901 expand giving interference fixation to the bone along the inner walls of the drill hole 16122. Once the screw 16128 is fully seated, secure fixation of the bone plate 16124 to the bone 16120 is established.

Figure 17A:
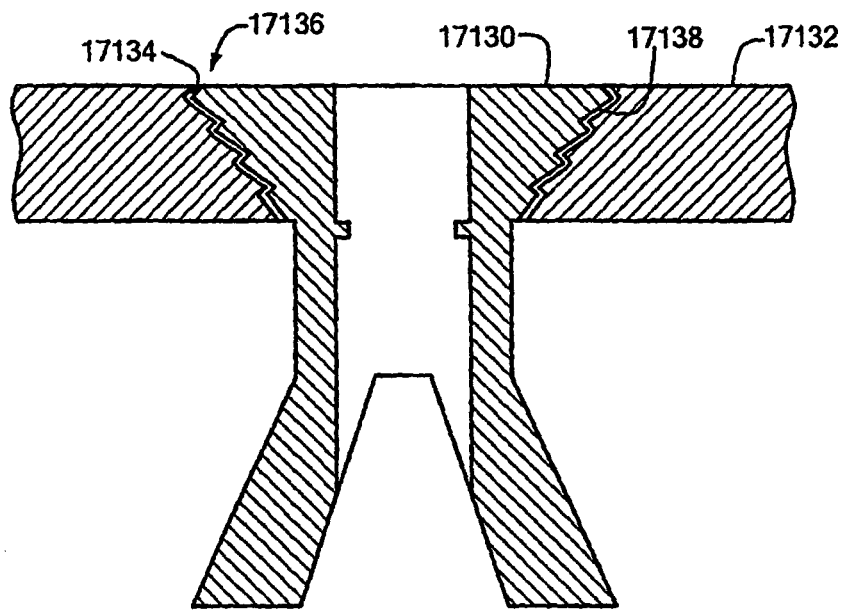
FIG. 17A is a cross-sectional side view of a locking plate and FAD.

Referring now to FIG. 17A an embodiment of a FAD 17130 used with a locking plate 17132 is shown. Locking plate 17132 is similar to bone plate 17124 shown in FIG. 16, except that the hole 17136 in locking plate 17132 has threaded, tapered side walls 17134. The threaded tapered side walls 17134 mate with a threaded external surface 17138 of FAD 17130. In this embodiment the FAD 17130 is inserted into the hole 17136 and rotated a predetermined amount to securely mate the FAD 17130 within the locking plate 17132. As shown, a top surface of the inserted FAD 17130 is generally coplanar with the top surface of the locking plate 17132.

Figure 17B:
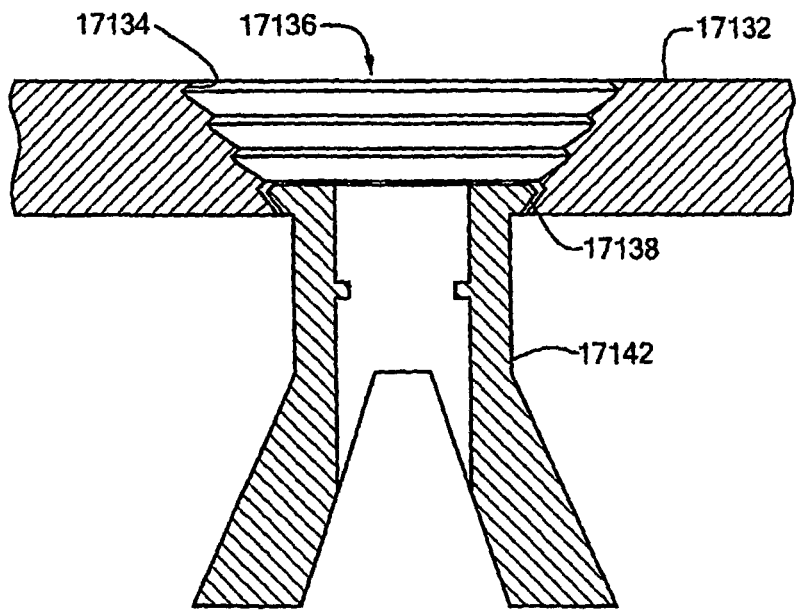
FIG. 17B is a cross-sectional side view of the locking plate and recessed FAD.

Referring now to FIG. 17B an embodiment of a FAD 17142 which is also used with a locking plate 17132 is shown. The threaded tapered side walls 17134 of hole 17136 in locking plate 17132 mate with a threaded external surface 17138 of FAD 17142. In this embodiment the FAD 17142 is inserted into the hole 17136 and rotated a predetermined amount to securely mate the FAD 17142 within the locking plate 17132. A top surface of the inserted FAD 17142 is recessed within hole 17136. This allows for a screw (not shown) inserted into FAD 17142 to have it's top surface be generally co-planar with the top surface of locking plate 17132 when the screw is completely inserted into the FAD 17142.

Figure 18:
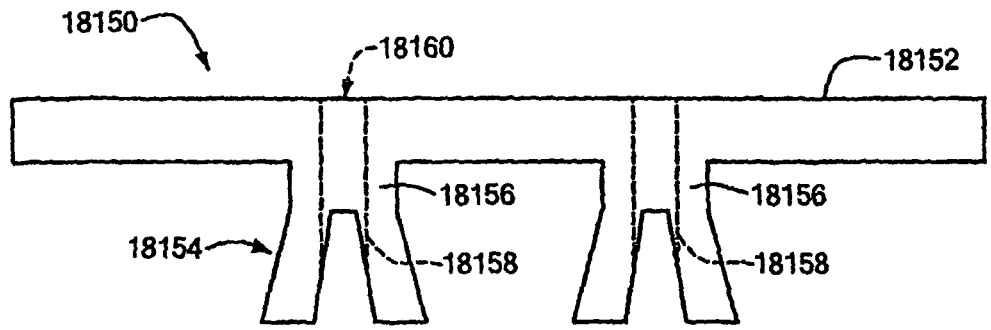
FIG. 18 is side view of a FAD integrated with a bone plate.
Figure 19A:
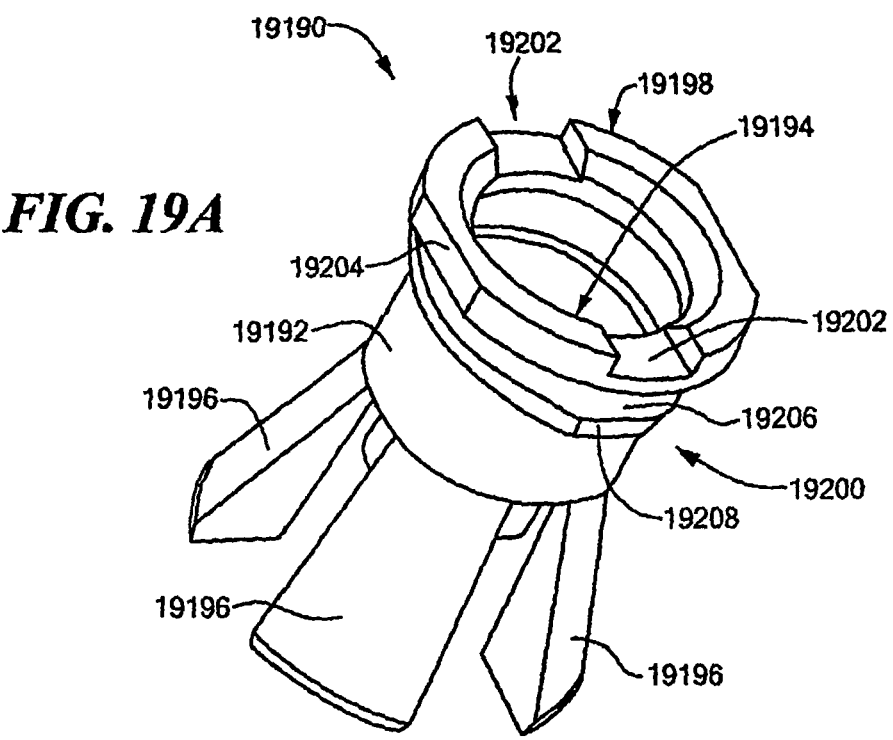
FIGS. 19A and 19B are isometric views of a FAD having a release-cam mechanism.
Figure 19B:
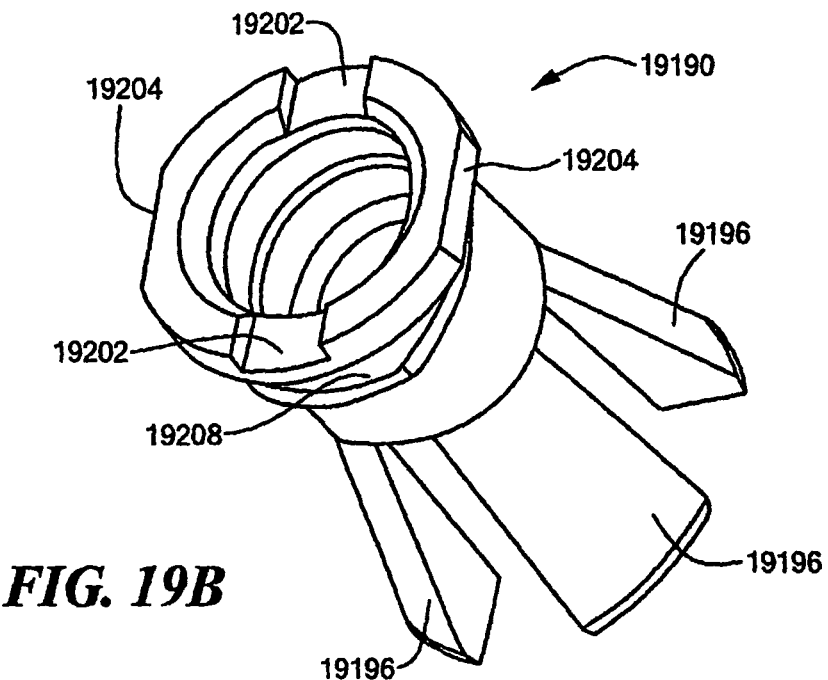
Figure 19C:
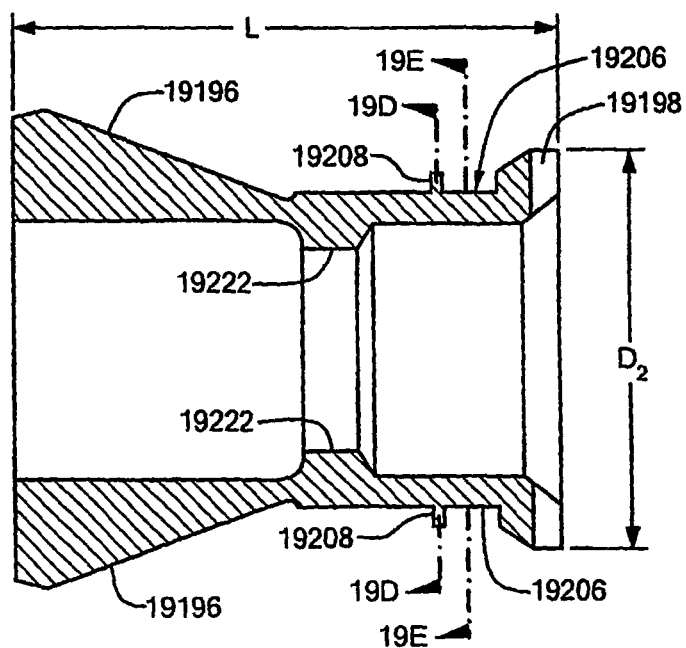
FIG. 19C is a cross-sectional side view of the FAD of FIGS. 19A and 19B.
Figure 19H:
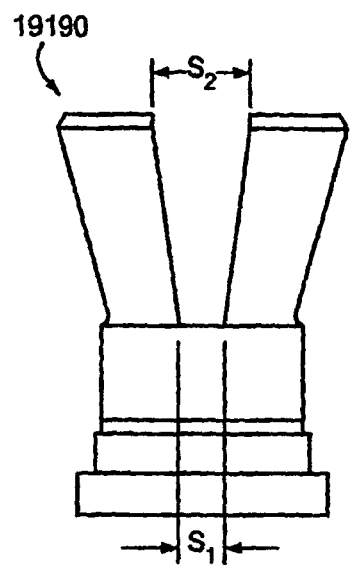
FIG. 19D is a cross-sectional view taken across lines 19D-19D of FIG. 19C.
FIG. 19E is a cross-sectional view taken across lines 19E-19E of FIG. 19C.
FIG. 19F is a side view of the expanded portion of the FAD of FIG. 19C.
FIG. 19G is a side view of the tab portion of the FAD of FIG. 19C, FIGS. 19H and 19I are additional views the FAD of FIGS. 19A and 19B.
Figure 19I:
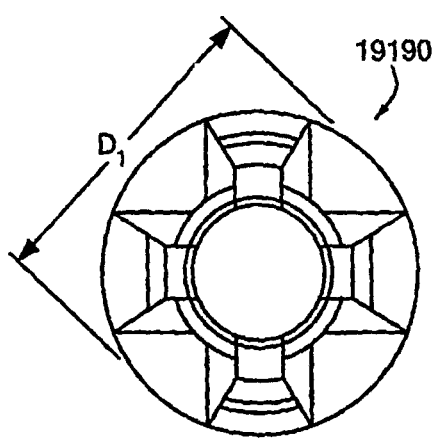

Referring now to FIG. 18, a device 17150 is shown which comprises at least one FAD portion and a bone plate portion integrated together as a single unitary device. The device 17150 includes a bone plate portion 17152 and one or more FAD portions 17154. A FAD portion 17154 includes a sleeve 17156, flanges 17158, and a core 17160. This device 17150 replaces a combination of a bone plate and separate FAD devices with a single unitary device providing similar functionality.

Referring now to FIGS. 19A-19I in which like elements are provided having like reference designations throughout the several views, another embodiment of a FAD 19190 is shown. The FAD in this embodiment is similar to FAD 1490 described above in conjunction with FIGS. 14A-14D but has some additional features including a release cam lock mechanism as will be described below. The FAD 19190 includes a sleeve 19192, a core 19194, flanges 19196 and a collar 19198, generally similar to FADs described above and a release cam lock mechanism 19200.

The Collar 19198 is provided having a pair of openings 19202. The openings 19202 are provided having a size and shape selected to accept a removal tool. In this particular example, the openings 19202 are provided having a rectangular-slot shape which accepts a flat tip of a removal tool. This aids in placing the device 19190 in proper alignment within a bone plate hole during insertion and removal of the device 19190.

During initial insertion of the device 19190 in a bone plate having an oval hole, the holes 19202 are aligned with the major (i.e. the longer) axis of the oval hole of the plate. This alignment insures that the device 19190 will seat properly in the bone plate during insertion as it is aligned with the oval shape of the locking mechanism 19200 beneath the collar 19198. With screw insertion and seating, the device 19190 rotates into a locked position on the plate and the holes 19202 show the orientation of the device 19190 to have rotated in the direction of the minor (i.e. the shorter) axis of the oval hole in the bone plate.

If the device 19190 and a screw have been inserted and it is desired to remove them, during the removal process the screw is withdrawn (either partially of fully) and once the screw is withdrawn from the device, the removal tool can be used to re-orient the openings 19202 of the device 19190 so they are once again aligned with the major axis of the oval hole in the bone plate. This insures that the device 19190 is no longer locked onto the plate and can be safely removed.

Flat surfaces 19204 on the collar 19198 are present to allow use of an anti-rotation tool if needed during supplement insertion and removal. The anti-rotation tool is a device used to prevent the device 19190 from rotating during the screw insertion and removal processes. The flat surfaces also provide a visual cue to properly align the device 19190 during insertion and removal of the device 19190. Similar to the slot 19202 in the collar 19198, the flat collar surfaces 19204 are aligned with the major axis of an oval hole in a bone plate during initial insertion and just prior to removal. This alignment insures that the device 19190 is no longer locked onto the plate as occurs when the supplement rotates slightly with screw insertion and seating as will become apparent from the description of FIG. 20 hereinbelow.

In this particular embodiment, the locking mechanism 19200 includes the collar 19198, one or more cam or cam regions 19206 beneath the collar 19198 and a tab 19208 which is below the collar 19198 and expansion regions 19206. In the embodiment shown in FIGS. 19A-19H, two cam regions 19206 are shown (best seen in FIG. 19E). The cam regions 19206 are provided in a cam arrangement with an offset from the device centerline by approximately 0.002 inches.

In one exemplary embodiment, the length $L_1$ (FIG. 19E) is in the range of about 0.188 to about 0.190 inches and the about and the length $L_2$ (FIG. 19E) is in the range of about 0.166 inches to about 0.168 inches. Also the lengths $L_3$ (FIG. 19D) and $L_4$ (FIG. 19D) of the tab region are in the range of about 0.190 to about 0.200 inches and in the range of about 0.164 to about 0.166 inches, respectively.

The expansion areas can be provided by having a portion of the sleeve 19192 made to have an oval shape or by having a portion of the sleeve 19192 made to have a cam-type arrangement as described above.

Also, as can be seen by comparing FIGS. 19D and 19E, the cam regions 19206 are slightly misaligned with the tabs 19208. This slight misalignment allows the tab 19208 to move underneath the plate (e.g. plate 20216 in FIG. 20) prior to the cam regions 19206 contacting a surface of the hole in the compression plate. This prevents further rotation of the FAD in the hole of the compression plate. In one embodiment, for a FAD having an overall length of about 0.3 inches (i.e. length from a top surface of the collar to a bottom surface of a flange), the thickness $T_1$ of the cam regions 19206 is in the range of about 0.032 inches and the thickness $T_2$ of the tabs 19208 is in the range of about 0.009 inches. Other thickness and axis lengths for the cam and tab regions may also be used depending upon the needs of any particular application. In one embodiment the major axes of the cam regions and tabs are offset by about three and on-half degrees although offsets in the range of about one to about thirty degrees may be used depending upon a variety of factors including the size of the FAD (including the lengths of the major and minor axes of both the cam region and tabs) as well as the lengths of the major and minor axes of the hole in the compression plate (or other structure) in which the FAD will be disposed.

As will be described below in conjunction with FIG. 20, when the device 19190 is inserted the device 19190 rotates with screw insertion and the tab 19208 feeds underneath the plate (e.g. plate 20216 in FIG. 20). This prevents the device 19190 from moving up and down within the plate hole and insures proper contact of the plate and device 19190. The cam region 19206 is positioned with respect to the tab 19208 such that upon rotation of the device, the cam region 19206 contacts an inner wall or surface (e.g. wall 20214a in FIG. 20) of the plate hole just after the tab 19208 feeds under the plate (e.g. plate 20216 in FIG. 20).

Because the length of the major axis of the cam region 19206 is longer than the length of the minor axis of the oval hole in the plate, further rotation of the device 19190 is prevented. However, the long axes for both the oval expansion and the tabs are short enough relative to the long axis of the oval plate hole to allow easy seating of the supplement during insertion of the device (i.e. both the tab and the expansion have to fit and the length of the major axis for the tab is slightly greater that the length of the major axis for the expansion).

It should be appreciated that the device 19190 may also be provided having features above such as flat (rather than beveled) internal and/or external collar surfaces. Also, the FAD 19190 may be provided having a bone in-growth treatment such as that described above. As mentioned above, the bone in-growth treatment could be a coating that is applied to the FAD, or could be realized as a treatment which is performed on the FAD to result in a textured surface which promotes bone in-growth to aid in securing the FAD to the bone structure. The bone in-growth treatment could be applied to at least a portion of one or more flanges 19196 (either inner or outer flange surfaces), at least a portion of the collar 19198, at least a portion of the sleeve 19192 or a combination thereof. The use of a FAD having a bone in-growth treatment applied thereto is particularly useful in scenarios where the bone may not have a large amount of mass for a FAD to attach to or where the FAD will be used as part of a structure that may support a lot of movement or weight, for example in securing a replacement hip socket to a pelvic bone.

In one exemplary embodiment, the FAD 19190 has an overall length L (FIG. 19C) of about 0.340 inches, a lower diameter $D_1$ (FIG. 191) in the range of about 0.254 inches, a flange diameter $D_2$ (FIG. 19C) of about 0.250 in. and slot openings $S_1$ (FIG. 19H) in the range of about 0.039 inches and $S_2$ (FIG. 19H) in the range of about 0.090 inches. Other lengths, diameters and slot sizes may, of course, also be used. The particular length and overall upper (i.e. collar) and lower (i.e. flange) diameters to be use in any particular application will be determined in accordance with a variety of factors including but not limited to the length and diameter of screws being inserted. Likewise, the particular size of slot openings to be used in any application will be determined in accordance with a variety of factors including but not limited to the length and overall diameter of the FAD as well as the length and diameter of screws being inserted into the FAD.

Figure 20:
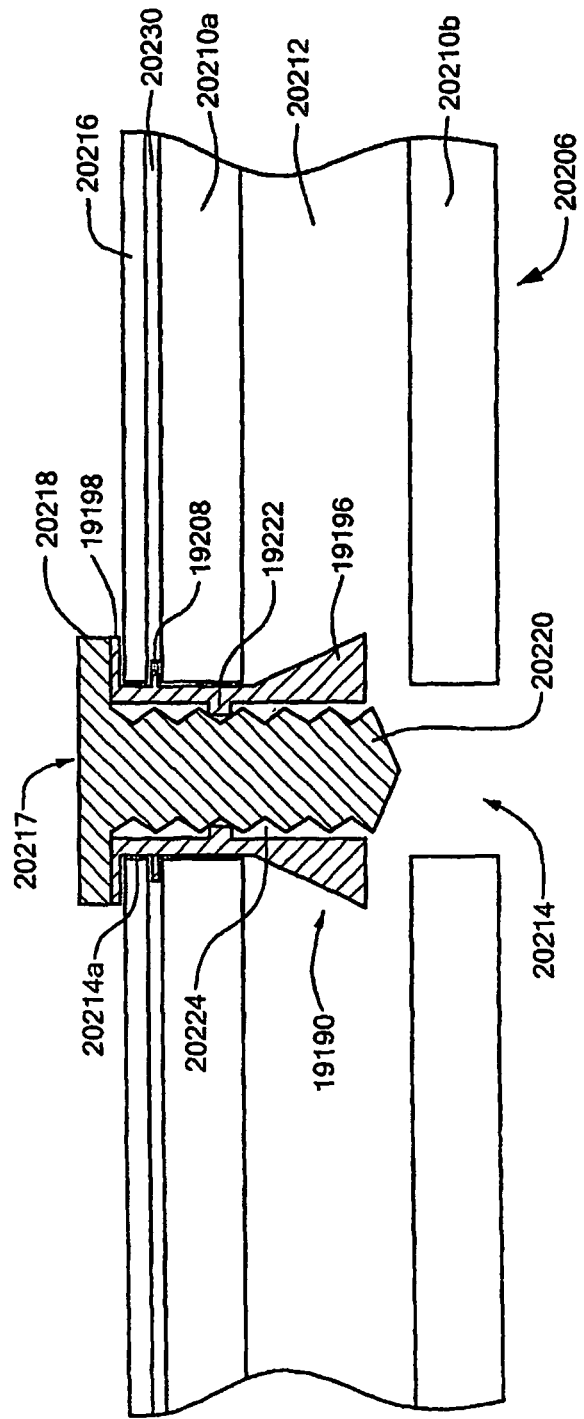
FIG. 20 is a cross-sectional view of a FAD inserted in a bone.

Referring now to FIG. 20, in which like elements of FIGS. 19A-19G are provided having like reference designations, a portion of a bone 20206 is shown to include an upper bone region 20210a, a lower bone region 20210b and a space region 20212 between the upper and lower bone regions 20210a, 20210b. A hole 20214 is provided through both the upper and lower bone regions 20210a, 20210b. Thus, the hole 20214 may be referred to as a "through hole" meaning that the hole provides a path through the entire bone 20206.

It should be appreciated, of course, that the hole 20214 need only pass through one bone portion (e.g. either bone portion 20210a or 20210b). Those of ordinary skill in the art will appreciate how to determine whether the hole 20214 should be provided to pass through only one of the bone regions 20210a, 20210b or whether it should pass through all regions of a bone (e.g. through both regions 20210a, 20210b of bone 20206.

A plate 20216 (e.g. a bone or compression plate) having an hole therein is disposed over the bone portion 20210a with the plate hole aligned with the hole 20214 in the bone portion 20210a. Once the plate hole and bone hole 20214 are aligned, the device 19190 is disposed in the hole 20214. The device 19190 can then be turned such that the collar 19198 engages a first surface of the plate 20216 and the tab 19208 engages a second surface of the plate.

In this particular embodiment, the hole 20214 in the plate 20216 is provided having an oval shape and the major axis of the cam region 19206 (most clearly seen in FIG. 19E) of the device 19190 is longer than the minor axis of the oval hole in the plate 20216. By making the major axis of the cam region 19206 of the device 19190 longer than the minor axis of the oval hole in the plate and by providing the cam region 19206 in a predetermined spatial relationship with respect to the tabs 19208, once the tabs 19208 engage the surface of the plate 20216, the cam region 19206 prevents further rotation of the device 19190 in the hole 20214.

A screw 20217 having a head portion 20218 and a body portion 20220 is disposed in the device 19190. Insertion of the screw in the device 19190 causes the flanges 19196 to open and secure the device 19190 in the hole and in particular in the space region 20212 of the bone 20206. The device 19190 also includes the thread region 19222 which engages threads 20224 provided in the screw body 20220. The screw threads 20224 engage the thread 19222 which, in combination with the opened flanges 19196, allows the screw 20217 to be securely coupled to the bone 20206.

A space 20230 may exist between a bottom surface of the plate and a surface of the bone 20210b, however, this space 20230 has substantially no impact on the ability of FAD 19190, plate 20216 or screw 20217 to serve their respective intended functions.

Having described preferred embodiments of the invention it will now become apparent to those of ordinary skill in the art that other embodiments incorporating these concepts may be used. Accordingly, it is submitted that the invention should not be limited to the described embodiments but rather should be limited only by the spirit and scope of the appended claims. All publications and references cited herein are expressly incorporated herein by reference in their entirety.

The invention claimed is:

1. A fixation augmentation device (FAD) for emplacement in a hole in a bone and adapted to secure a bone plate to the bone, the FAD comprising:
  a generally tubular body having a first end and a second end, the body having an axial bore extending from the first end to the second end for receiving a screw therein;
  an integral peripheral collar disposed at the first end of the body;
  two cam regions disposed at the first end of the body, distal to the collar, the cam regions having a non-circular shape;
  two tabs disposed at the first end of the body, distal to the cam regions and proximal to the second end
  a plurality of elongate flanges disposed at the second end of the body; and
  a plurality of hinge sections connecting the plurality of elongate flanges to the second end of the body whereby the plurality of elongate flanges can pivot outwardly relative to the body in response to a screw being inserted into the axial bore of the body.

2. The fixation augmentation device of claim 1 wherein the collar has a peripheral surface with an oval shape.

3. The fixation augmentation device of claim 1 wherein the collar has a non-uniform width.

4. The fixation augmentation device of claim 1 wherein an outer surface of the collar is tapered.

5. The fixation augmentation device of claim 1 wherein an inner surface of the collar is tapered.

6. The fixation augmentation device of claim 1 wherein each of the plurality of elongate flanges has a generally flat outer surface.

7. The fixation augmentation device of claim 1 wherein each of the plurality of elongate flanges has an outer surface characterized by a generally circular curvature in cross-section.

8. The fixation augmentation device of claim 1 wherein the bore is defined by an inner surface of the body, and further wherein a section of the inner surface is provided with a screw thread adapted to receive and mate with a screw that is inserted into the bore from the first end of the body, the section of the inner surface being spaced from the first end of the body and extending over a fraction of the length of the inner surface.

9. The fixation augmentation device of claim 8 wherein the section of the inner surface is located substantially adjacent to the hinge sections.

10. The fixation augmentation device of claim 1 further comprising a bone plate with a hole extending therethrough, the bone plate hole having a predetermined size selected to receive the tubular body therein, and further where the bone plate hole is formed so as to prevent passage therethrough of the collar.

11. The fixation augmentation device of claim 10 wherein the hole in the bone plate has a non-circular shape.

12. The fixation augmentation device of claim 1 wherein the collar, cam region and tabs form part of a release-cam lock mechanism.

13. The fixation augmentation device of claim 1 wherein the collar has a non-circular shape.

14. The fixation augmentation device of claim 13 wherein the body has a circular shape cross-section.

15. The fixation augmentation device of claim 1 wherein the body, the hinge sections and the flanges are formed as an integral unit, and further wherein the body has a fixed wall thickness and the hinge section has a thickness less than the fixed wall thickness.

16. The fixation augmentation device of claim 1 wherein each of the flanges has an outer surface, and further wherein the flanges are formed so that the outer surfaces thereof extend substantially parallel to the bore in the absence of any force urging the flanges to pivot outwardly relative to the body.

17. The fixation augmentation device of claim 1 wherein each of the flanges has first and second ends and first and second side surfaces that extend lengthwise of the device, the first ends of the flanges being attached to the hinge sections and the first and second side surfaces being angled so as to diverge from one another with increasing distance from the hinge sections.

18. A fixation augmentation device for emplacement in a hole in a bone and adapted to secure a plate with a pass-through hole to the bone, the device comprising:

a hollow body characterized by first and second opposite ends and internal and external lengthwise-extending surfaces, with the internal surface defining an axial bore and the external surface having a fixed maximum diameter that is smaller than the pass-through hole in the plate and also smaller than the hole in the bone to which the plate is to be secured;

a peripheral collar formed at the first end of the body, the collar protruding from the body with a maximum diameter that exceeds the hole in the bone to which the plate is to be secured and the minimum diameter of the pass-through hole in the plate;

two cam regions disposed at the first end of the body, distal to the collar, cam regions having a non-circular shape;

two tabs disposed at the first end of the body, distal to the cam regions and proximal to the second end a plurality of elongate flanges hingedly attached to the second end of the body by hinge sections formed integral with the body and the flanges, the flanges having inner and outer surfaces, with the inner surfaces defining an elongate opening coaxial with the bore and the outer surfaces collectively defining a circle having a diameter not exceeding the hole in the bone, whereby the flanges can be inserted in the hole in the bone; and the internal surface of the body having a screw thread extending along the axial bore for receiving a screw sized to cause the flanges to pivot outwardly relative to the body as the screw is advanced in the axial bore and into the elongate opening.

19. The fixed augmentation device of claim 18 wherein the screw thread extends over only a portion of the length of the internal surface.

20. The fixation augmentation device of claim 18 further including a screw sized to be inserted into the axial bore in interlocking engagement with the screw thread and to cause the flanges to pivot outwardly relative to the body as the screw is advanced in the axial bore.

21. The fixation augmentation device of claim 20 wherein the flanges have outer ends remote from the body, and the screw has a head and a shank with the shank having a length sufficient for it to extend beyond the outer ends of the flanges when the head is engaged with the plate.

22. The fixation augmentation device of claim 18 further comprising a bone plate with a pass-through hole extending therethrough, the bone plate hole having a predetermined size selected to receive the hollow body therein, and further where the bone plate hole is formed so as to prevent passage therethrough of the collar.

23. The fixation augmentation device of claim 22 wherein the bone plate hole has a non-circular shape.

24. A fixation augmentation device in combination with a screw and a bone plate intended to be secured to a bone by the device and the screw;

the screw having a head and a threaded shank;
the bone plate having a pass-through hole therein; and
the fixation augmentation device being adapted for insertion through the pass-through hole into a hole in a bone;
the fixation augmentation device comprising:
(a) a hollow body characterized by first and second opposite ends and internal and external lengthwise-extending surfaces, with the internal surface defining an axial bore with a screw thread and the external surface having a generally cylindrical shape with a fixed maximum diameter that is smaller than the pass-through hole in the plate and also smaller than the hole in the bone to which the plate is to be secured;
(b) a plurality of elongate flanges hingedly attached to the second end of the body by hinge sections formed integral with the body and the flanges, the flanges having inner and outer surfaces, with the inner surfaces defining an elongate opening in axial alignment with the bore and the outer surfaces collectively defining a circle having a diameter not exceeding the hole in the bone and smaller than the diameter of the pass-through hole in the plate, whereby the flanges can be inserted through the pass-through hole into the hole in the bone;

(c) a peripheral collar formed at the first end of the body, the collar protruding from the body with a maximum diameter that exceeds the hole in the bone to which the plate is to be secured and a minimum diameter of the pass-through hole in the plate;

(d) two cam regions disposed at the first end of the body, distal to the collar, the cam regions having a non-circular shape; and (e) two tabs disposed at the first end of the body, distal to the cam regions and proximal to the second end the head of the screw being large enough to make interfering engagement with the first end of the body and the threaded shank being sized to be insertable into the axial bore and to make a screw connection with the screw thread, with the threaded shank having a length sufficient for it to engage the inner surfaces of the flanges as it is advanced in the bore and to thereby force the flanges to pivot outwardly relative to the body, whereby the flanges can be brought into engagement with the portion of the bone that defines the bone hole, the engagement being sufficient to secure the device and the plate to the bone.

25. The fixation augmentation device of claim 24 wherein the pass-through hole in the bone plate has a non-circular shape.

\* \* \* \* \*